(12) United States Patent
Ortiz et al.

(10) Patent No.: US 8,460,186 B2
(45) Date of Patent: Jun. 11, 2013

(54) METHODS AND DEVICES FOR PROVIDING ACCESS THROUGH TISSUE TO A SURGICAL SITE

(75) Inventors: Mark S. Ortiz, Milford, OH (US);
Brandon L. Livingston, Mason, OH (US); Dhananjay V. Patil, Mumbai (IN);
Mark S. Zeiner, Mason, OH (US);
Theodore J. DiMagno, Penfield, NY (US); Edgar V. Menezes, Jacksonville, FL (US); Aron O. Zingman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 781 days.

(21) Appl. No.: 12/636,205

(22) Filed: Dec. 11, 2009

(65) Prior Publication Data
US 2011/0144449 A1    Jun. 16, 2011

(51) Int. Cl.
*A61B 1/32* (2006.01)

(52) U.S. Cl.
USPC ............................................... 600/216

(58) Field of Classification Search
USPC ........................... 606/190–194; 600/201–216
See application file for complete search history.

(56) References Cited

U.S. PATENT DOCUMENTS

| | | | |
|---|---|---|---|
| 3,397,699 A | 8/1968 | Kohl | |
| 4,022,191 A | 5/1977 | Jamshidi | |
| 4,368,577 A | 1/1983 | Babb | |
| 4,608,977 A | 9/1986 | Brown | |
| 4,809,694 A | 3/1989 | Ferrara | |
| 5,031,634 A | 7/1991 | Simon | |
| 5,053,042 A | 10/1991 | Bidwell | |
| 5,100,387 A | 3/1992 | Ng | |
| 5,122,122 A * | 6/1992 | Allgood | 604/174 |
| 5,201,742 A | 4/1993 | Hasson | |
| 5,232,451 A | 8/1993 | Freitas et al. | |
| 5,235,987 A | 8/1993 | Wolfe | |

(Continued)

FOREIGN PATENT DOCUMENTS

| | | |
|---|---|---|
| EP | 577400 A1 | 1/1994 |
| WO | 9636283 A1 | 11/1996 |

(Continued)

OTHER PUBLICATIONS

U.S. Appl. No. 12/339,473, filed Mar. 6, 2009, Methods and Devices for Providing Access Into a Body Cavity.

(Continued)

*Primary Examiner* — Eduardo C Robert
*Assistant Examiner* — Tara Carter
(74) *Attorney, Agent, or Firm* — Nutter McClennen & Fish LLP

(57) ABSTRACT

Methods and devices are provided for providing access through tissue to a surgical site. Generally, the methods and devices allow adjustment of a surgical access port's longitudinal length. In one embodiment, a surgical access port is provided that includes a housing having a cannula distally extending therefrom. The housing can be configured to cut a proximal portion of the cannula to adjust a longitudinal length of the cannula and hence of the surgical access port. In another embodiment, a surgical access port is provided that includes a cannula formed of a plurality of modular segments removably coupled together. One or more of the segments can be configured to be removable from the cannula to change the cannula's longitudinal length.

18 Claims, 18 Drawing Sheets

U.S. PATENT DOCUMENTS

| | | |
|---|---|---|
| 5,312,417 A | 5/1994 | Wilk |
| 5,316,014 A | 5/1994 | Livingston |
| 5,320,111 A | 6/1994 | Livingston |
| 5,330,437 A | 7/1994 | Durman |
| 5,330,497 A | 7/1994 | Freitas et al. |
| 5,342,315 A | 8/1994 | Rowe et al. |
| 5,431,676 A | 7/1995 | Dubrul et al. |
| 5,468,248 A | 11/1995 | Chin et al. |
| 5,494,039 A | 2/1996 | Onik et al. |
| 5,569,205 A | 10/1996 | Hart et al. |
| 5,628,732 A | 5/1997 | Antoon, Jr. et al. |
| 5,647,373 A | 7/1997 | Paltieli et al. |
| 5,697,946 A | 12/1997 | Hopper et al. |
| 5,707,359 A | 1/1998 | Bufalini |
| 5,836,913 A | 11/1998 | Orth et al. |
| 5,857,999 A | 1/1999 | Quick et al. |
| 5,868,673 A | 2/1999 | Vesely |
| 5,882,340 A | 3/1999 | Yoon |
| 5,911,707 A | 6/1999 | Wolvek et al. |
| 5,916,175 A | 6/1999 | Bauer et al. |
| 5,941,889 A | 8/1999 | Cermak |
| 5,954,670 A | 9/1999 | Baker |
| 5,957,888 A | 9/1999 | Hinchliffe |
| 5,984,930 A | 11/1999 | Maciunas et al. |
| 6,017,356 A | 1/2000 | Frederick et al. |
| 6,030,365 A | 2/2000 | Laufer |
| D422,706 S | 4/2000 | Bucholz et al. |
| 6,048,321 A | 4/2000 | McPherson et al. |
| 6,110,182 A | 8/2000 | Mowlai-Ashtiani |
| 6,162,196 A | 12/2000 | Hart et al. |
| 6,195,577 B1 | 2/2001 | Truwit et al. |
| 6,203,499 B1 | 3/2001 | Imling |
| 6,216,029 B1 | 4/2001 | Paltieli et al. |
| 6,231,565 B1 | 5/2001 | Tovey et al. |
| 6,231,585 B1 | 5/2001 | Takahashi et al. |
| 6,236,875 B1 | 5/2001 | Bucholz et al. |
| 6,245,028 B1 | 6/2001 | Furst et al. |
| 6,283,942 B1 | 9/2001 | Staehlin et al. |
| 6,361,499 B1 | 3/2002 | Bates et al. |
| 6,379,307 B1 | 4/2002 | Filly et al. |
| 6,400,979 B1 | 6/2002 | Stoianovici et al. |
| 6,443,960 B1 | 9/2002 | Brabrand et al. |
| 6,445,943 B1 | 9/2002 | Ferre et al. |
| 6,451,042 B1 | 9/2002 | Bonutti |
| 6,468,226 B1 | 10/2002 | McIntyre, IV |
| 6,475,152 B1 | 11/2002 | Kelly, Jr. et al. |
| 6,490,467 B1 | 12/2002 | Bucholz et al. |
| 6,501,981 B1 | 12/2002 | Schweikard et al. |
| 6,529,765 B1 | 3/2003 | Franck et al. |
| 6,535,756 B1 | 3/2003 | Simon et al. |
| 6,539,121 B1 | 3/2003 | Haskell et al. |
| 6,546,279 B1 | 4/2003 | Bova et al. |
| 6,547,782 B1 | 4/2003 | Taylor |
| 6,551,270 B1 | 4/2003 | Bimbo et al. |
| 6,665,554 B1 | 12/2003 | Charles et al. |
| 6,671,962 B2 | 1/2004 | Watamura |
| 6,687,531 B1 | 2/2004 | Ferre et al. |
| 6,723,106 B1 | 4/2004 | Charles et al. |
| 6,731,966 B1 | 5/2004 | Spigelman et al. |
| 6,752,812 B1 | 6/2004 | Truwit |
| 6,770,027 B2 | 8/2004 | Banik et al. |
| 6,782,288 B2 | 8/2004 | Truwit |
| 6,783,524 B2 | 8/2004 | Anderson |
| 6,785,572 B2 | 8/2004 | Yanof et al. |
| 6,808,492 B2 | 10/2004 | Snyder |
| 7,021,173 B2 | 4/2006 | Stoianovici et al. |
| 7,056,329 B2 | 6/2006 | Kerr |
| 7,076,106 B2 | 7/2006 | Haskell et al. |
| 7,083,626 B2 | 8/2006 | Hart et al. |
| 7,163,525 B2 | 1/2007 | Franer |
| 7,371,227 B2 | 5/2008 | Zeiner |
| 2003/0100814 A1 | 5/2003 | Kindlein |
| 2003/0208207 A1 | 11/2003 | Layer |
| 2003/0229338 A1 | 12/2003 | Irion et al. |
| 2004/0082969 A1 | 4/2004 | Kerr |
| 2004/0185453 A1 | 9/2004 | Myerson et al. |
| 2004/0230161 A1 | 11/2004 | Zeiner |
| 2004/0254426 A1 | 12/2004 | Wenchell |
| 2004/0260246 A1 | 12/2004 | Desmond |
| 2005/0119685 A1 | 6/2005 | Smith |
| 2005/0222582 A1 | 10/2005 | Wenchell |
| 2006/0069414 A1 | 3/2006 | Imran et al. |
| 2006/0135972 A1* | 6/2006 | Zeiner .......................... 606/167 |
| 2006/0149137 A1 | 7/2006 | Pingleton et al. |
| 2006/0200185 A1* | 9/2006 | Marchek et al. .............. 606/191 |
| 2006/0247499 A1 | 11/2006 | Butler et al. |
| 2006/0247673 A1 | 11/2006 | Voegele et al. |
| 2007/0185453 A1 | 8/2007 | Michael et al. |
| 2007/0260121 A1 | 11/2007 | Bakos et al. |
| 2007/0260273 A1 | 11/2007 | Cropper et al. |
| 2008/0086080 A1 | 4/2008 | Mastri et al. |
| 2008/0086167 A1 | 4/2008 | Mastri et al. |
| 2008/0249373 A1 | 10/2008 | Wenchell |
| 2008/0255519 A1 | 10/2008 | Piskun et al. |
| 2009/0005799 A1 | 1/2009 | Franer et al. |
| 2009/0105659 A1 | 4/2009 | Bettuchi et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |

FOREIGN PATENT DOCUMENTS

| | | |
|---|---|---|
| WO | 0041759 A1 | 7/2000 |
| WO | 0062689 A1 | 10/2000 |
| WO | 0108563 A2 | 2/2001 |
| WO | 2005097019 A2 | 10/2005 |
| WO | 2005097234 A2 | 10/2005 |
| WO | 2006057982 A2 | 6/2006 |

OTHER PUBLICATIONS

U.S. Appl. No. 12/399,482, filed Mar. 6, 2009, Methods and Devices for Providing Access Into a Body Cavity.

U.S. Appl. No. 12/399,547, filed Mar. 6, 2009, Surgical Access Devices and Methods Providing Seal Movement in Predefined Paths.

U.S. Appl. No. 12/399,625, filed Mar. 6, 2009, Methods and Devices for Providing Access Into a Body Cavity.

U.S. Appl. No. 12/420,146, filed Apr. 8, 2009, Methods and Devices for Providing Access Into a Body Cavity.

U.S. Appl. No. 12/424,213, filed Apr. 15, 2009, Cannula With Sealing Elements.

U.S. Appl. No. 12/478,862, filed Jun. 5, 2009, Flexible Cannula Devices and Methods.

U.S. Appl. No. 12/478,882, filed Jun. 15, 2009, Multi-Planar Obturator With Foldable Retractor.

U.S. Appl. No. 12/479,030, filed Jun. 5, 2009, Retractor With Integrated Wound Closure.

U.S. Appl. No. 12/479,096, filed Jun. 5, 2009, Interlocking Seal Components.

U.S. Appl. No. 12/479,293, filed Jun. 5, 2009, Methods and Devices for Providing Access Through Tissue to Surgical Site.

U.S. Appl. No. 12/479,395, filed Jun. 5, 2009, Methods and Devices for Accessing a Body Cavity Using Surgical Access Device With Modular Seal Components.

U.S. Appl. No. 12/512,542, filed Jul. 30, 2009, Methods and Devices for Providing Access Into a Body Cavity.

U.S. Appl. No. 12/512,568, filed Jun. 30, 2009, Methods and Devices for Providing Access Into a Body Cavity.

U.S. Appl. No. 12/636,184, filed Dec. 11, 2009, Methods and Devices for Providing Access Through Tissue to a Surgical Site.

U.S. Appl. No. 12/636,191, filed Dec. 11, 2009, Methods and Devices for Providing Access Through Tissue to a Surgical Site.

U.S. Appl. No. 12/636,020, filed Dec. 11, 2009, Inverted Conical Expandable Retractor.

U.S. Appl. No. 12/636,023, filed Dec. 11, 2009, Inverted Concical Expandable Retractor With Coil Spring.

U.S. Appl. No. 12/635,754, filed Dec. 11, 2009, Methods and Devices for Providing Access Into a Body Cavity.

U.S. Appl. No. 12/635,762, filed Dec. 11, 2009, Methods and Devices for Providing Access Into a Body Cavity.

U.S. Appl. No. 12/635,990, filed Dec. 11, 2009, Methods and Devices for Accessing a Body Cavity.
U.S. Appl. No. 12/623,018, filed Nov. 20, 2009, Discrete Flexion Head for Single Port Device.
U.S. Appl. No. 12/636,174, filed Dec. 11, 2009, Methods and Devices for Providing Access Through Tissue to a Surgical Site.

International Search Report and Written Opinion for PCT/US2010/059622 dated Mar. 10, 2011.
U.S. Appl. No. 12/636,232, filed Dec. 11, 2009.

* cited by examiner

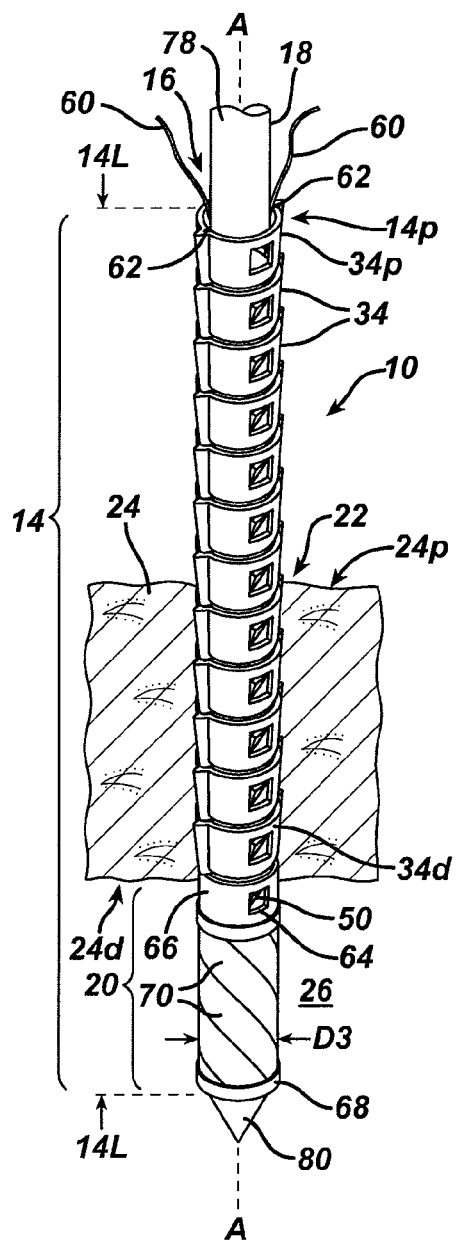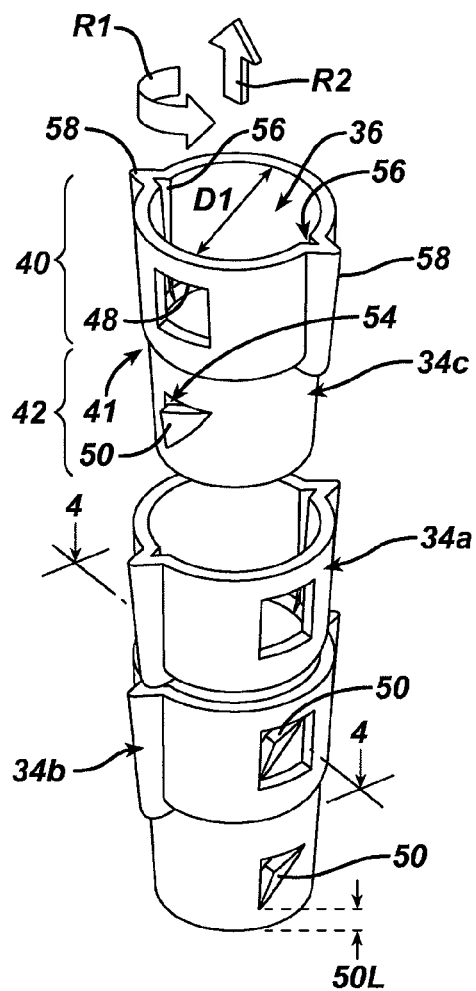
FIG. 1
FIG. 2

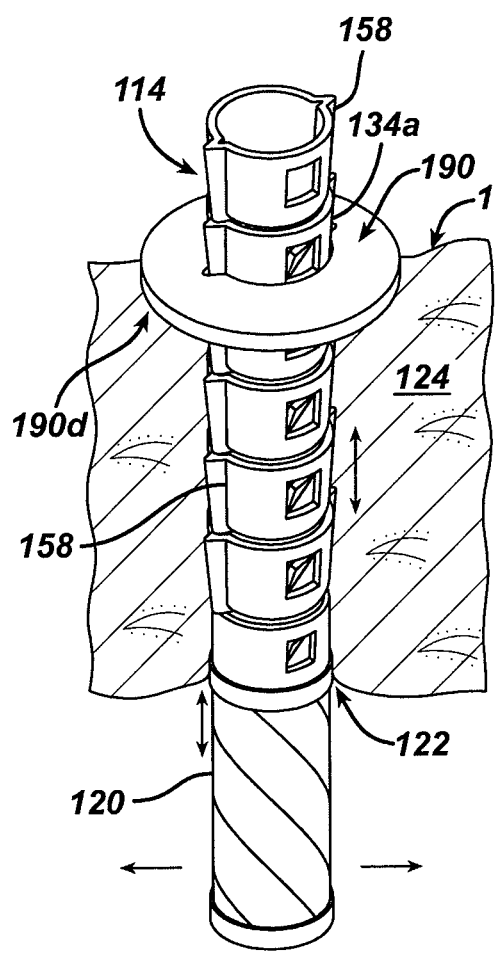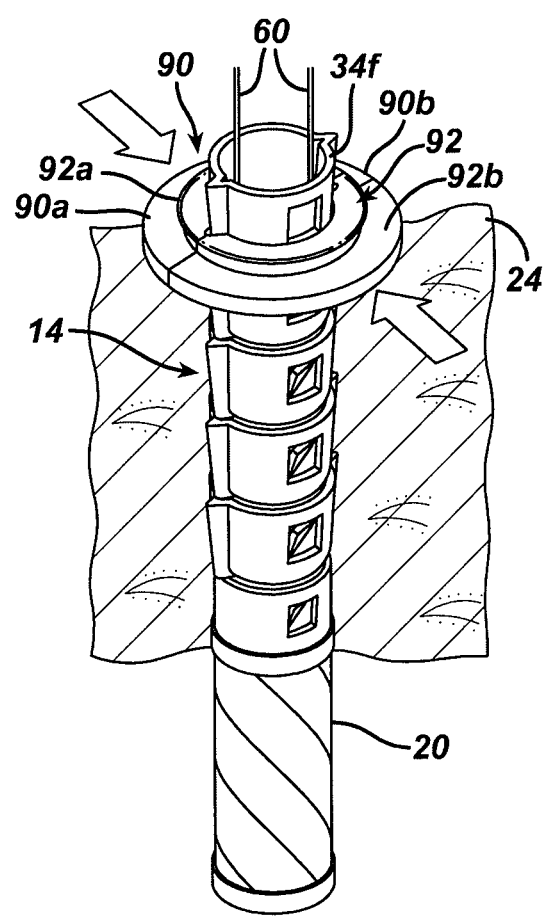

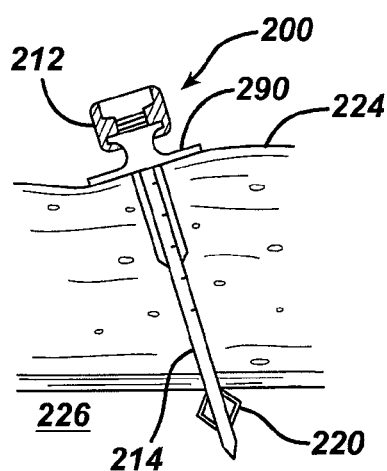
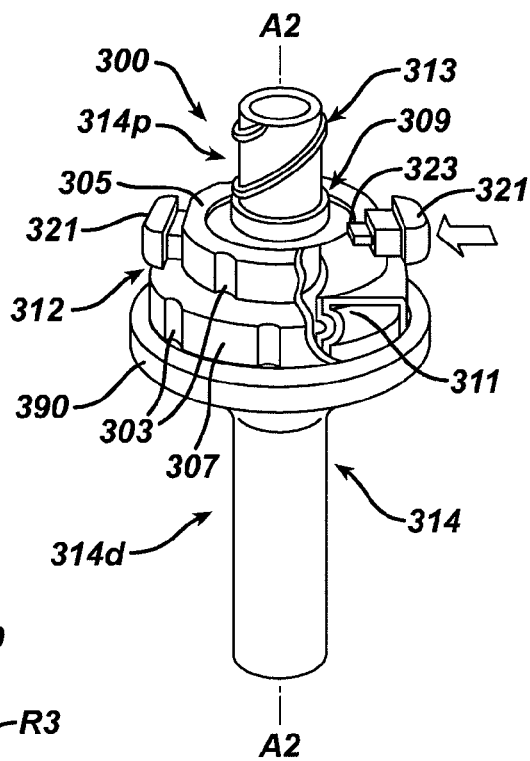
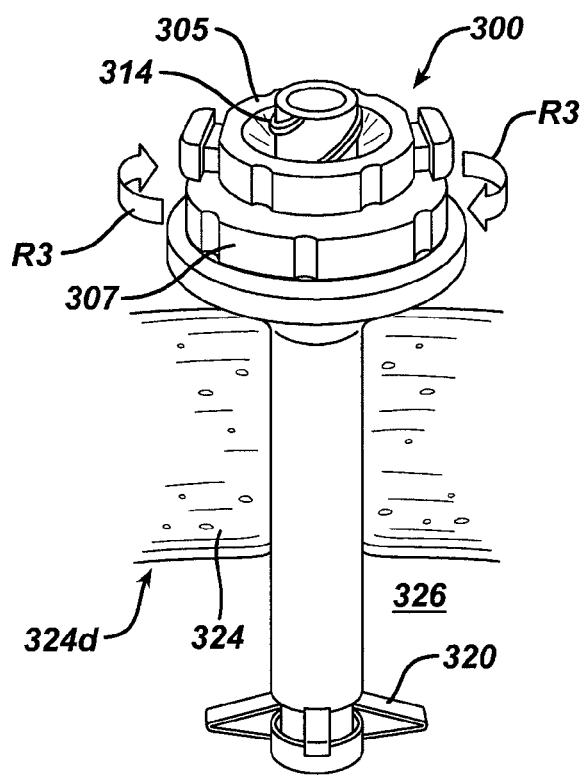

FIG. 39
FIG. 40
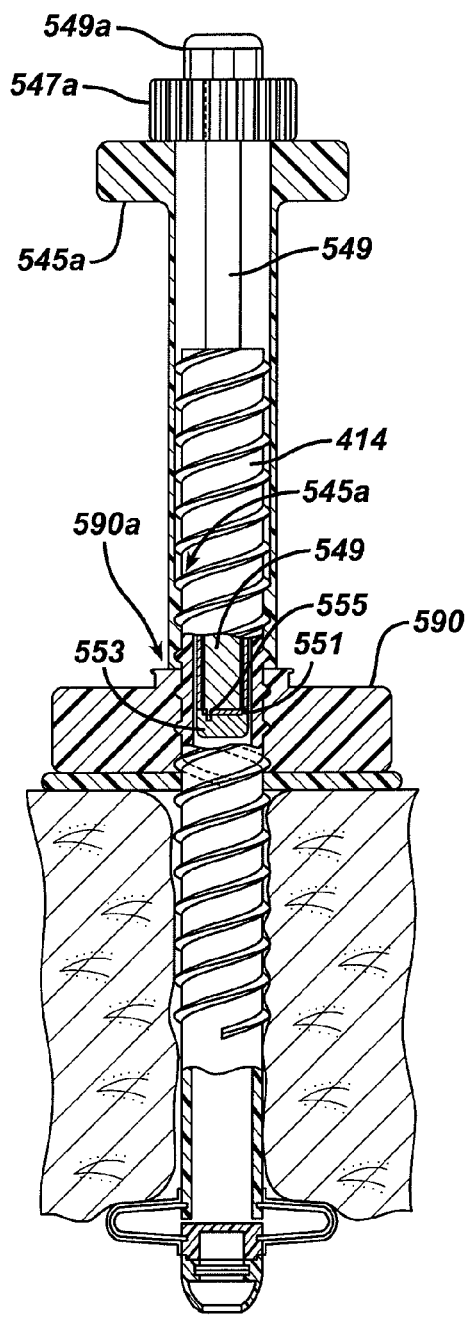
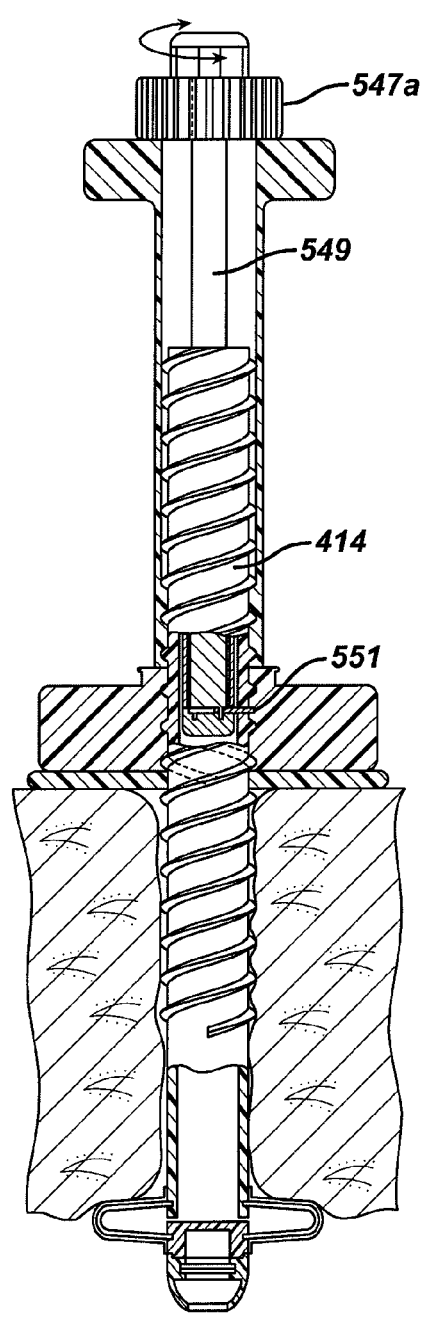

METHODS AND DEVICES FOR PROVIDING ACCESS THROUGH TISSUE TO A SURGICAL SITE

CROSS REFERENCE TO RELATED APPLICATIONS

The present application is being filed concurrently with U.S. application Ser. No. 12/636,232 entitled "Methods And Devices For Providing Access Through Tissue To A Surgical Site," which is incorporated by reference herein in its entirety.

FIELD OF THE INVENTION

The present invention relates to methods and devices for providing access through tissue to a surgical site.

BACKGROUND OF THE INVENTION

Access ports are widely used in medical procedures to gain access to anatomical cavities ranging in size from the abdomen to small blood vessels, such as veins and arteries, epidural, pleural and subarachnoid spaces, heart ventricles, and spinal and synovial cavities. The use of access ports has become more common as they provide minimally invasive techniques for establishing a portal for a number of procedures, such as those involving the abdominal cavity.

A trocar is one type of access post that is commonly used to provide a minimally invasive pathway for accessing a surgical site. Trocars generally include a cutting assembly or obturator that is disposed within an outer cannula. The sharp distal end of the cutting assembly, with the cannula disposed therearound, is urged through the skin until it enters the anatomical cavity being penetrated. The cutting assembly is then withdrawn from the cannula, which remains in place to provide a passageway through which access to the anatomical cavity is provided for other surgical devices, e.g., laparoscopic instruments such as graspers, dissectors, scissors, retractors, etc.

While effective, there can be many disadvantages when using a typical trocar assembly. For example, numerous types of procedures using a typical trocar assembly involve insufflation of the abdominal cavity with $CO_2$ gas to increase interior space for a surgical procedure. This is often achieved using an additional port to allow gas to be passed into a body cavity to provide pressure therein to maintain insufflation of the cavity. Maintaining insufflation can be difficult because the trocar can extend a distance above the skin and surface through which it is inserted depending on the length of the trocar, which could create a gap through which insufflation fluid can escape. Additionally, the trocar could move relative to the tissue in which it is inserted, such as when instruments are inserted therethrough into the cavity, which could affect insufflation as well as interfere with proper positioning of the instruments. Insufflation can be made even more difficult before the body cavity is inflated as there are organs and other vital structures that can be directly adjacent the puncture site where the trocar assembly is inserted through the tissue, and it is desirable to prevent damage to these structures during insertion of the trocar.

Accordingly, there is a need for improved methods and devices for providing access through tissue to a surgical site.

SUMMARY OF THE INVENTION

The present invention generally provides methods and devices for providing access through tissue to a surgical site. In one embodiment, an adjustable access device is provided including a cannula including a plurality of segments removably coupled to one another such that a mating connection between each of the plurality of segments forms a fluid tight seal and such that a length of the cannula is adjustable, and a collar slidably disposed on the cannula and configured to selectively engage one of the plurality of segments to allow adjustment of a distance between the collar and a distal end of the cannula. The cannula defines a working channel extending therethrough for receiving an instrument.

The device can also include a housing configured to mate to the collar. The housing can have at least one seal disposed therein that is configured to form at least one of a seal around an instrument disposed through the housing and a seal across the housing when no instrument is disposed therethrough.

The segments can have a variety of configurations. Each segment can optionally include an engagement feature to removably mate to an adjacent segment. The engagement feature can include at least one radially-extending protrusion configured to engage an opening in an adjacent segment. In some embodiments, each of the segments proximal to the one of the plurality of segments engaged by the collar can be removable from the one of the plurality of segments engaged by the collar and each of the plurality of segments distal to the collar. The segments located proximal to the one of the plurality of segments engaged by the collar can be rotatable about a longitudinal axis of the cannula to release the segments located proximal to the one of the plurality of segments engaged by the collar from the one of the plurality of segments engaged by the collar and each of the plurality of segments distal to the collar. An alignment feature of the collar can engage a complementary alignment feature of the one of the plurality of the segments to allow the segments proximal to the one of the plurality of segments engaged by the collar to be removed from the one of the plurality of segments engaged by the collar.

The device can have any number of variations. In some embodiments, the collar can have an alignment feature configured to align with a complementary alignment feature of the cannula such that the collar is only slidably disposable on the cannula in at least one predetermined orientation. An expandable anchor can be optionally coupled to the distal end of the cannula.

In another embodiment, an adjustable access device is provided that includes an elongate tube defining a fluid-tight inner passageway extending longitudinally therethrough, a collar having a central opening, and a housing configured to mate to the collar. The elongate tube includes a plurality of segments releasably coupled together and configured to be selectively removed from a proximal end of the elongate tube to reduce a longitudinal length of the elongate tube. The collar is configured to receive the elongate tube through the central opening such that each of the plurality of segments proximal to the collar is removable from a remainder of the plurality of segments to reduce the longitudinal length of the elongate tube. The housing has at least one seal disposed therein that is configured to form at least one of a seal around an instrument disposed through the housing and a seal across the housing when no instrument is disposed therethrough.

In some embodiments, an anchor can be coupled to a distal-most one of the plurality of segments. An actuator extending inside the elongate tube along a longitudinal length thereof can be configured to be actuated to move the anchor from a first configuration in which the anchor has a first outer diameter to a second configuration in which the anchor has a second outer diameter that is greater than the first outer diameter.

The plurality of segments can vary in any number of ways. The plurality of segments proximal to the collar can be removable as a singular unit from the remainder of the plurality of segments by rotating the plurality of segments proximal to the collar as a singular unit about a longitudinal axis of the elongate tube relative to the remainder of the plurality of segments. In some embodiments, each of the plurality of segments can have a distally-tapering shape such that when a distal end of one of the plurality of segments is inserted into a proximal end of another one of the plurality of segments a fluid-tight seal formed between the one of the plurality of segments and the other one of the plurality of segments. The device can optionally include one or more additional segments configured to be selectively attached to a terminal end of the elongate tube to increase the longitudinal length of the elongate tube.

In another embodiment, an adjustable access device is provided that includes a housing having a cannula extending distally therefrom, and an actuator on the housing configured to cut the cannula to adjust a length of the cannula. The housing and the cannula define a working channel extending therethrough for receiving an instrument. A distal portion of the housing can optionally include a compressible seal element comprising at least one of a gel or a foam.

In some embodiments, an anchor segment can be attached to a distal-most end of the cannula. The anchor segment can have a maximum outer diameter that is greater than a maximum outer diameter of the cannula.

The cannula can have a variety of configurations. For example, the cannula can include threads and be configured to rotate relative to the housing such that the threads on the cannula threadably move relative to the housing to move a proximal portion of the cannula proximal to the housing. The housing can be configured to form the threads on the cannula when the cannula rotates relative to the housing.

The actuator can also have a variety of configurations. The actuator can be configured to cut the cannula such that a proximal portion of the cannula can be removed from a distal remainder of the cannula. In some embodiments, the actuator can include a cutting mechanism contained within a fluid-tight interior cavity of the housing. The cannula can be configured to proximally advance relative to the housing such that a proximal portion of the cannula moves into the cavity. In some embodiments, the actuator can include at least one depressible tab coupled to the housing and configured to be depressed to cut the cannula.

In another aspect, a method of adjusting an access device is provided that includes inserting a plurality of cannulated segments removably coupled together and defining a fluid-tight tube through an opening in tissue such that a collar disposed around the tube and a proximal end of the tube are positioned outside the tissue and such that at least a distal end of the tube is disposed in a body cavity underlying the tissue, and removing each of the segments located proximal to the collar from the tube inserted through the opening in tissue such that a remainder of the tube extends through the opening in tissue with the collar disposed around the tube. The collar can be advanced toward the distal end of the tube before removing each of the segments located proximal to the collar.

The method can have any number of variations. Removing each of the segments located proximal to the collar from the tube can include rotating each of the segments located proximal to the collar relative to the remainder of the tube. Inserting the plurality of segments through the opening in tissue can include inserting an anchor coupled to a distal-most one of the segments through the opening in tissue in an unexpanded configuration. The anchor can be moved in the body cavity from the unexpanded configuration to an expanded configuration.

In another embodiment, a method of adjusting an access device is provided that includes positioning a cannula through an opening in tissue such that a distal end of the cannula is positioned in a body cavity underlying the tissue and such that a housing coupled to a proximal end of the cannula is positioned outside the tissue, proximally moving the cannula relative to the housing, and adjusting a length of the cannula by actuating the housing to cut the cannula. In some embodiments, positioning the cannula through the opening in tissue can include inserting the cannula through the opening in tissue with a substantially rigid obturator disposed in the cannula.

Proximally moving the cannula relative to the housing can include moving a proximal portion of the cannula to extend proximally above the housing such that the distal end of the cannula remains positioned in the body cavity and/or moving a proximal portion of the cannula from outside the housing into an internal cavity of the housing. Proximally moving the cannula relative to the housing can cause an anchor disposed at the distal end of the cannula to deploy within the body cavity and/or can compress a compressible seal element in a distal portion of the housing to create a fluid-tight seal between the housing and an outside surface of the tissue.

In another embodiment, a method of adjusting an access device is provided that includes inserting a cannula having a first longitudinal length through an opening in tissue such that a housing at a proximal end of the cannula is positioned above the tissue and such that a distal end of the cannula is positioned in a body cavity underlying the tissue, and moving the cannula in a proximal direction relative to the housing such that the cannula moves from the first longitudinal length to a second longitudinal length that is less than the first longitudinal length. In some embodiments, moving the cannula in the proximal direction can move a proximal portion of the cannula into an internal cavity of the housing to move the cannula from the first longitudinal length to the second longitudinal length.

Moving the cannula in the proximal direction can move a proximal portion of the cannula proximal to the housing, and moving the cannula to the second longitudinal length can include removing the proximal portion of the cannula from a distal remainder of the cannula. In some embodiments, moving the cannula to the second longitudinal length can include actuating an actuator coupled to the housing to cut the cannula to allow a proximal portion of the cannula to be removed from a distal remainder of the cannula. Actuating the actuator can include depressing at least one tab on the housing such that a cutting element coupled to the tab moves radially inward to cut the cannula.

BRIEF DESCRIPTION OF THE DRAWINGS

The invention will be more fully understood from the following detailed description taken in conjunction with the accompanying drawings, in which:

FIG. 1 is a perspective, partial cross-sectional view of one embodiment of a surgical access device including a cannula formed of a plurality of segments, the cannula being positioned within a tissue opening, having an obturator received therein, and having an anchor in an undeployed configuration at a distal end thereof;

FIG. 2 is a perspective view of three of the segments of FIG. 1;

FIG. 13 is a perspective, partially cross-sectional view of another embodiment of a surgical access device including a cannula formed of a plurality of segments, the cannula being positioned within a tissue opening, having a collar positioned therearound proximal to the tissue opening, and having an anchor in an undeployed configuration at a distal end thereof;

FIG. 14 is a perspective, partially cross-sectional view of the surgical access device of FIG. 12 with a collar positioned around the distal remainder of the cannula proximal to the tissue opening;

FIG. 20 is a side, cross-sectional view of the surgical access device of FIG. 18 with a proximal housing attached to the collar and the distal remainder of the cannula;

FIG. 21 is a perspective, partially cross-sectional view of another embodiment of a surgical access device including a housing having a cannula distally extending therefrom;

FIG. 22 is a perspective, partially cross-sectional view of the surgical access device of FIG. 21 with the cannula positioned within a tissue opening and the housing located proximal to the tissue opening, the housing being rotated to adjust a longitudinal length of the cannula and deploy an anchor at a distal end of the cannula;

FIG. 39 is a side, partially transparent, partially cross-sectional view of the cannula and collar of FIG. 38 with the cutting assembly mated to the cannula and the cutting assembly out of cutting engagement with the cannula;

FIG. 40 is a side, partially transparent, partially cross-sectional view of the cutting assembly, cannula, and collar of FIG. 39 with the cutting assembly in cutting engagement with the cannula;

DETAILED DESCRIPTION OF THE INVENTION

Figure 3:
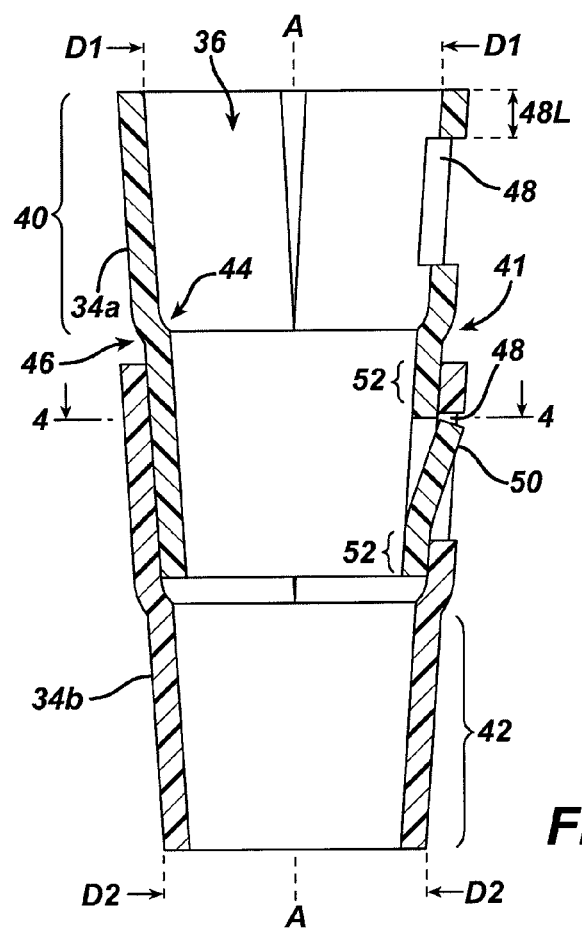
FIG. 3 is a side, cross-sectional view of two of the segments of FIG. 1 removably coupled together.
Figure 4:
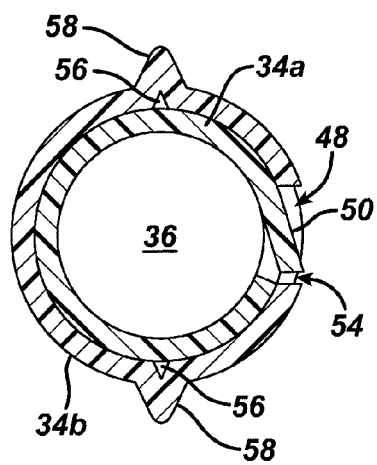
FIG. 4 is a cross-sectional view of the segments of FIG. 3.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are disclosed for providing access through tissue to a surgical site. In general, the methods and devices provide access through tissue to a body cavity underlying the tissue using a surgical access port configured to be secured within an opening in the tissue to allow access therethrough. In an exemplary embodiment, a surgical access port is provided that has an adjustable longitudinal length. In one exemplary embodiment, a surgical access port can include a housing having a cannula distally extending therefrom. The housing can be configured to cut a proximal portion of the cannula to adjust a longitudinal length of the cannula and hence of the surgical access port. In another exemplary embodiment, a surgical access port can include a cannula formed of a plurality of modular segments removably coupled together. One or more of the segments can be configured to be removable from the cannula to change the cannula's longitudinal length. Because tissue thicknesses can vary, a surgical access port having an adjustable longitudinal length can allow the surgical access port to be appropriate for use with a variety of tissue thicknesses and can facilitate secure positioning of the surgical access port within tissue. A surgical access port with an adjustable longitudinal length can minimally extend into a body cavity underlying the tissue where the surgical access port could harm body structures within the body cavity and/or interfere with instruments performing a surgical procedure. The surgical access port's longitudinal length can be selectively adjusted after it is positioned within an opening in tissue, thereby allowing the longitudinal length to be tailored to a particular tissue's thickness with a reduced need to guess or pre-measure a tissue's thickness.

The various surgical access devices disclosed herein can include an elongate tubular member, cannula, or other member for forming a pathway through tissue, generally referred to as a "cannula." The cannula can extend distally from a proximal housing configured to be at least partially disposed outside a patient's body, and it can be configured to be positioned within an opening in a patient's body, such as through skin. The proximal housing can include one or more sealing ports that can each define working channels extending through the housing and aligned with the cannula. A person skilled in the art will appreciate that the cannula can include one or more sealing ports, in addition or in alternative to one or more sealing ports in the housing. Any and all of the surgical access devices described herein can also include various other features, such as one or more ventilation ports to allow evacuation of smoke during procedures that utilize cautery, and/or one or more insufflation ports through which the surgeon can insufflate the abdomen to cause pneumoperitenium, as described by way of non-limiting example in U.S. Patent Publication No. 2006/0247673 entitled "Multi-port Laparoscopic Access Device" filed Nov. 2, 2006, which is hereby incorporated by reference in its entirety. The insufflation port can be located anywhere on the device, can have any size, and can accept a leur lock or a needle, as will be appreciated by those skilled in the art.

In use, and as also further discussed below, the surgical access devices disclosed herein can provide access to a patient's body cavity. At least a portion of the cannula can be positionable within an opening in a patient's body such that a distal portion of the cannula extends into a patient's body cavity and at least a portion of the housing is positioned adjacent to the patient's skin on an exterior of the patient's body. In some embodiments, the device may not include a housing, in which case at least a proximal portion of the cannula and/or a collar positioned around the cannula can be positioned adjacent to the patient's skin on an exterior of the patient's body when another portion of the cannula is positioned within an opening in a patient's body. A lumen in the cannula and the housing can form a pathway through the opening in a patient's body so that surgical instruments can be inserted from outside the body to an interior body cavity. The elasticity of the skin of the patient can assist in the retention of the cannula in the body opening or incision made in the body. The cannula can be placed in any opening within a patient's body, whether a natural orifice or an opening made by an incision. In one embodiment, the cannula can be substantially flexible, e.g., formed of a flexible material, so that it can easily be maneuvered into and within tissue as needed. Non-limiting examples of flexible materials that can form the cannula include polyethylene, silicone, polypropylene, polycarbonate, and flexible elastomers. In other embodiments, the cannula can be substantially rigid or substantially semi-rigid. In some embodiments, the cannula can include a substantially rigid elongate tube with a substantially flexible overmold.

Typically, during surgical procedures in a body cavity, such as the abdomen, insufflation is provided through the surgical access device to expand the body cavity to facilitate the surgical procedure. Thus, in order to maintain insufflation within the body cavity, most surgical access devices include at least one seal disposed therein to prevent air and/or gas from escaping when surgical instruments are inserted therethrough. Various sealing elements are known in the art, but typically the surgical access device can include at least one instrument seal that forms a seal around an instrument disposed therethrough, but otherwise does not form a seal when no instrument is disposed therethrough, at least one channel seal or zero-closure seal that seals the working channel created by the sealing port when no instrument is disposed therethrough, or a combination instrument seal and channel seal that is effective to both form a seal around an instrument disposed therethrough and to form a seal in the working channel when no instrument is disposed therethrough. A person skilled in the art will appreciate that various seals known in the art can be used including, e.g., duckbill seals, cone seals, flapper valves, gel seals, diaphragm seals, lip seals, iris seals, etc. A person skilled in the art will also appreciate that any combination of seals can be included in any of the embodiments described herein, whether or not the seal combinations are specifically discussed in the corresponding description of a particular embodiment.

As mentioned above, a surgical access device can be configured to adjust in longitudinal length by removal and/or addition of one or more modular segments forming a cannula of the device. In an exemplary embodiment illustrated in FIG. 1, a surgical access device 10 can be configured to be positioned within an opening 22 in tissue 24 to provide access to a body cavity 26 underlying the tissue 24 and allow a surgical instrument such as an obturator 18 to be slidably and removably inserted therethrough to perform a surgical procedure. The device 10 can have a variety of sizes, shapes, and configurations, and as shown in FIG. 1 can include a tubular member in the form of a cannula 14 having a selectively adjustable longitudinal length 14L. The device 10 can also include a housing (not shown) and/or a collar (not shown) from which the cannula 14 distally extends, as discussed further below. An anchor, anchor segment, or anchor 20, generally referred to as an "anchor," can optionally be located at a distal end 14d of the cannula 14 and can assist in securing the device 10 within the tissue opening 22, as discussed further below. The anchor 20 can be fixedly or removably coupled to the segments 34 and can be configured to self-deploy, or the obturator 18 or other deployment mechanism can be configured to deploy the anchor 20, as also discussed further below. The cannula 14, and the housing and/or the collar, if present, can define a working channel 16 extending through the device 10 and being configured to slidably and removably receive the obturator 18 and/or any number of other surgical instruments therein.

As in the illustrated embodiment, the cannula 14 can include a plurality of beads, modules, or segments 34, generally referred to as "segments," removably coupled together such that one or more of the segments 34 can be removed from one or both of the cannula's proximal and distal ends 14p, 14d to adjust the cannula's longitudinal length 14L. In this way, the segments 34 can be configured to allow the cannula 14 to be positioned within tissue of any thickness, e.g., in a range of about 1-7 cm thick, without the cannula 14 extending a substantial longitudinal length proximally beyond the tissue's proximal surface 24p or a substantial longitudinal length distally beyond the tissue's distal surface 24d.

The segments 34, the obturator 18, and the anchor 20 can each have a variety of sizes, shapes, and configurations. The segments 34 can be the same or different from any of the cannula's other segments 34. In the illustrated embodiment, each of the segments 34 is identical. The segments 34 can be composed of any one or more flexible and/or rigid materials, although the segments 34 in the illustrated embodiment are rigid, e.g., formed of a rigid material such as stainless steel. Non-limiting examples of flexible materials that can form the segments 34 include puncture-resistant polymers such as isoprene, polyethylene, and polypropylene. Optionally, at least a distal-most one of the segments 34d forming the cannula 14 can be formed of a material more rigid than a material forming other ones of the segments 34, which can help facilitate insertion of the cannula 14 through the tissue opening 22 and retention of the cannula 14 therein. The segments 34 can each have any longitudinal length, e.g., in a range of about 1 to 2 cm.

Each of the segments 34 can include a substantially cylindrical body having an inner lumen 36 extending therethrough such that when the segments 34 are connected and axially aligned together along a longitudinal axis A of the cannula 14, also a longitudinal axis of the working channel 16 and the device 10, define at least a portion of the device's working channel 16. In this way, when multiple segments 34 are attached together, the cannula 14 can have a substantially cylindrical shape. Although the segments 34 in the illustrated embodiment each have substantially circular cross-sections, the segments 34 can have any cross-sectional shape, e.g., ovular, square, rectangular, etc. The segment's body can include proximal and distal portions 40, 42 configured to allow engagement and release of adjacent segments from one another.

In the illustrated embodiment, as shown in FIGS. 1-4, the proximal and distal portions 40, 42 can be configured to removably mate the segments 34 together. As in the illustrated embodiment, the proximal portion 40 can be configured as a female member and the distal portion 42 can be configured as a male member configured to be disposed within the proximal portion 40. In other words, the distal portion 42 of one segment, e.g., a first segment 34a, can be configured to be receivable in the inner lumen 36 of the proximal portion 40 of an adjacent segment, e.g., a second segment 34b, such that segments 34 connected together overlap with or nest with one another to form an elongate tubular member defining a continuous inner lumen, e.g., at least a portion of the device's working channel 16. In this way, any number of segments 34 can be selectively attached together to form the cannula 14 to suit a particular surgical application.

The segment's proximal and distal portions 40 can have a variety of sizes, shapes, and configurations, such as shown in FIGS. 1-4 with the proximal portion 40 having an inner diameter D1 at its proximal-most end, e.g., a diameter of the inner lumen 36 at a proximal-most end of the segment 34, and the distal portion 42 having an outer diameter D2 at its distal-most end, e.g., an outer diameter at a distal-most end of the segment 34. The distal-most outer diameter D2 can be less than the proximal-most inner diameter D1. In this way, the distal portion 42 of one segment 34, e.g., the first segment 34a, can be inserted into the proximal portion 40 of another segment 34, e.g., the second segment 34b. The segment's inner lumen 36 and the segment's outer diameter can optionally correspondingly taper in a distal direction in the proximal and distal portions 40, 42, as shown in FIGS. 2 and 3, which can facilitate insertion of a segment's distal portion 42 into another segment's proximal portion 40. The distal portion 42 can have a wall thickness less than a wall thickness of the proximal portion 40 to help minimize variation between inner and outer diameters of a cannula formed of a plurality of the segments 34.

The segments 34 can include one or more complementary mating features configured to facilitate secure attachment of adjacent segments. Although the mating features can have a variety of configurations, e.g., snap-fit elements, complementary threads, an interference fit, etc., in the illustrated embodiment, the segments 34 include a mating feature in the form of a snap fit mechanism. Each segment 34 can include an opening or window 48, generally referred to as a "window," formed through a sidewall thereof in the proximal portion 40 and a protrusion, tab, or flange 50, generally referred to as a "tab," extending radially outward from a sidewall thereof in the distal portion 42. The window 48 of one segment, e.g., the second segment 34b, can be configured to receive the tab 50 of another segment, e.g., the first segment 34a, therein such that the tab 50 snaps into the window 48 to mate the two segments 34a, 34b together by snap fit. The window 48 is illustrated as a square opening through the segment's sidewall, but the window 48 can have any shape and can extend only partially through the segment's sidewall. Similarly, the tab 50 is shown in the illustrated embodiment as a triangular member, but the tab 50 can have any shape configured to engage the window 48. Although the window 48 and the tabs 50 can be formed anywhere, in an exemplary embodiment, each segment's window 48 can be located a distance 48L distally beyond the segment's proximal-most end, and each segment's tab 50 can be located a distance 50L proximally beyond the segment's distal-most end. In this way, when one of the segments 34 is attached to another segment 34, a fluid tight seal can be formed between the segments 34 as shown in FIG. 3. In other words, with the proximal and distal portions 40, 42 having complementary sizes and shapes, an interference fit between adjacent proximal and distal portions 40, 42 can be provided in regions 52 proximally above and distally below a tab 50 engaged with an window 48. Although the windows 48 and the tabs 50 are configured in the illustrated embodiment to snap fit together such that a gap 54 exists between an engaged opening 48 and tab 50, in some embodiments, the windows 48 and the tabs 50 can be configured to snap fit or otherwise engage one another without such a gap 54 so as to provide a fluid-tight seal therebetween.

Each segment 34 can optionally include a stop mechanism configured to facilitate secure mating of adjacent segments 34. The stop mechanism can have a variety of sizes, shapes, and configurations. In the illustrated embodiment, at a junction 41 of the proximal and distal portions 40, 42, each segment 34 can optionally include an inner circumferential lip 44 configured as a stop mechanism to engage the distal-most end of another segment 34 being inserted therein and prevent further distal movement thereof. Additionally or alternatively, at the junction 41 of the proximal and distal portions 40, 42, each segment 34 can include an outer circumferential lip 46 configured as a stop mechanism to engage the proximal-most end of the segment 34 in which it is being inserted. The stop mechanism can also be configured to facilitate fluid-tight sealing of the working channel 16 extending through the segments 34 forming the cannula 14 because, e.g., the distal-most end of the first segment 34a contacting the inner circumferential lip 44 of the second segment 34b and/or the outer circumferential lip 46 of the first segment 34a contacting the proximal-most end of the second segment 34b can indicate that the first and second segments 34a, 34b are properly mated together without gaps therebetween through which fluid can enter or exit the working channel 16 extending through the cannula 14. The outer circumferential lip 46 of the first segment 34a and/or the proximal-most end of the second segment 34b in which it is being inserted can include at least one gripping feature (not shown), e.g., a textured surface, complementary protrusions and depressions, etc., formed thereon to facilitate secure attachment of the segments 34a, 34b.

An external surface of each of the segments 34, e.g., on an external surface of the proximal portion 40, can optionally include at least one gripping feature (not shown) formed thereon, e.g., a textured surface, finger or instrument depressions, at least one thread, etc., that can be configured to facilitate the segment's retention within tissue and/or facilitate gripping of segments 34 when attaching or detaching segments 34.

The segments 34 can each include an alignment mechanism configured to indicate alignment of adjacent segments 34 to facilitate correct rotational orientation of segments 34 being connected to one another. In the illustrated embodiment, the alignment mechanism includes a feature in the form of at least one longitudinal rib 58 extending radially outward from a sidewall of each of the segments 34 and defining a longitudinal channel 56 within the segment's inner lumen 36. Although the segments 34 are each illustrated with two ribs 58 spaced equidistantly from each other around the segment's perimeter, e.g., 180° apart from one another, and each having a triangular cross-section, a segment can include any number of ribs having any cross-sectional shape and spaced any distance apart from one another. The longitudinal ribs 58 can be configured to indicate alignment of a segment 34 relative to another segment 34 such that when ribs 58 on adjacent segments 34 are axially aligned with one another, the proximal and distal portions 40, 42 of the segments 34 can be mated as discussed above with the windows 48 and tabs 50 on the segments 34 properly aligning so as to engage one another to connect the segments 34 together.

The device 10 can include an anti-rotation feature configured to prevent rotation of at least one segment 34 relative to at least one other of the segments 34 to thereby adjust the longitudinal length 14L of the cannula 14, and thus a longitudinal length of the device 10. In the illustrated embodiment, the anti-rotation feature includes the ribs 58, as discussed further below.

As discussed above, any number of segments 34 can be attached together by joining together proximal and distal portions 40, 42 of the segments 34 to form the cannula 14. Similarly, any number of the segments 34 can be detached from either or both proximal and distal ends of the cannula 14 to reduce the cannula's longitudinal length 14L. Generally, as shown in FIG. 2, a proximal-most segment 34c can be rotated clockwise, as shown by a first directional arrow R1, relative to the adjacent distal segment 34a to disengage the segment's tab 50 from the window 48 of the adjacent segment 34a. A person skilled in the art will appreciate that the segments 34 can be configured such that counterclockwise rotation of the proximal-most segment 34c can disengage the segment's tab 50 from the window 48 of the adjacent segment 34a. With the window 48 and the tab 50 disengaged, the proximal-most segment 34c can be moved in a proximal direction, as shown by a second directional arrow R2, to remove the proximal-most segment's distal portion 42 from the first segment's proximal portion 40, thereby releasing the proximal-most segment 34c from the first segment 34a. Optionally, a plurality of segments, anchors, collars, and/or housings can be provided as part of a kit that can be assembled and/or disassembled to form a surgical access device tailored for a particular surgical application. Removal of segments 34 from the cannula 14 is discussed further below.

When a plurality of segments 34 are attached together to form the cannula 14, the one or more channels 56 in each of the segments 34 can axially align with one another and define one or more longitudinal channels 62 extending through the cannula 14. The cannula's longitudinal channels 62 can each be configured to receive a surgical instrument inserted therethrough and/or be configured to seat a cable, string, thread, band, ribbon, strip, or wire 60, generally referred to as a "string." Although the device 10 includes a number of strings 60 equal to a number of cannula channels 62, the device 10 can include any number of strings 60, and each of the cannula's channels 62 can be configured to seat any number of strings 60. The channels 62 each have a triangular cross-sectional shape, although they can have any cross-sectional shape. Generally, the strings 60 can be configured to extend along the device 10 and to move the anchor 20 between deployed and undeployed configurations, as discussed further below.

The anchor 20 can have a variety of sizes, shapes, and configurations. The anchor 20, also illustrated in FIGS. 5 and 6, can be configured to be coupled to the distal-most one of the segments 34d and can have a variety of sizes, shapes, and configurations. Although the anchor 20 can be fixedly attached to the segments 34, e.g., by welding, integrally formed parts, etc., or removably mated to the segments 34 using any mating feature, in the illustrated embodiment, the anchor 20 is removably mated to the distal-most one of the segments 34d through a snap fit mechanism. The anchor 20 can include a window 64 formed through a sidewall in a proximal rim 66 thereof, the window 64 being configured to releasably receive the tab 50 of the distal-most segment 34d, similar to that discussed above regarding the windows 48 and the tabs 50 of the segments 34.

Figure 5:
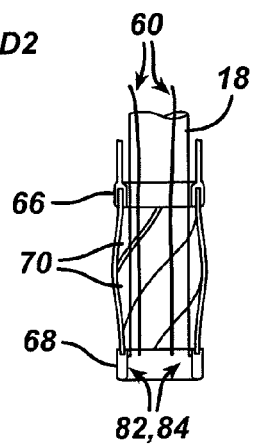
FIG. 5 is a side, cross-sectional view of the anchor of FIG. 1 in an undeployed configuration and having the obturator received therein.

The anchor 20 can include the proximal rim 66 and a distal rim 68 having an expandable mid-portion extending therebetween. The expandable mid-portion can have a variety of configurations, such as shown in the illustrated embodiment with a plurality of flexible cables, strings, threads, bands, ribbons, strips, or wires 70, generally referred to as "wires," spaced longitudinally apart from one another and extending between the rims 66, 68 with terminal ends of each of the wires 70 attached to the proximal and distal rims 66, 68. The proximal and distal rims 66, 68 can each include a rigid ring-shaped member as in the illustrated embodiment, but they can each have a variety of sizes, shapes, and configurations. The wires 70 can spiral between the proximal and distal rims 66, 68 at least when the anchor 20 is in the undeployed configuration, as shown in FIGS. 1 and 5. The wires 70 can be radially arranged and spaced equidistantly or any other distance apart from one another, and can be configured to collapse when the anchor 20 moves from the first configuration to the second configuration, as discussed further below.

Optionally, a flexible outer sheath (not shown) can be disposed around the wires 70 to help protect the wires 70 and prevent the wires 70 from snagging on tissue or other matter. The sheath can optionally include a gripping feature, e.g., a textured surface, a non-slip coating, etc., configured to help grip tissue and reduce slippage of the anchor 20 against the tissue when the anchor 20 is deployed and abuts the tissue.

Figure 11:
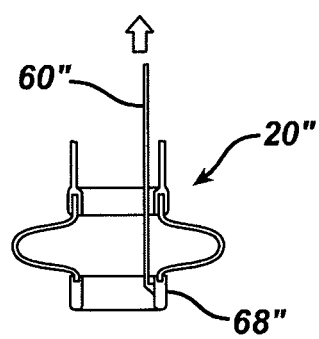
FIG. 11 is a side, cross-sectional view of the anchor of FIG. 10 in a deployed configuration.

Generally, the anchor 20 can be configured to change shapes to facilitate securement of the device 10 within tissue. As in the illustrated embodiment, the anchor 20 can be configured to move between a first, undeployed configuration, shown in FIGS. 1, 5, 12, and 14 in which the anchor 20 has a first outer diameter D3, and a second, deployed configuration, shown in FIGS. 6, 11, and 15, in which the anchor 20 has a second, larger outer diameter D4. The first outer diameter D3 can be equal to or less than a maximum outer diameter of the cannula 14, while the second outer diameter D4 can be greater than the cannula's maximum outer diameter. Because the tissue opening 22 in which the device 10 can be positioned can have a diameter substantially equal to the cannula's maximum outer diameter, the anchor's larger second outer diameter D4 can help prevent the anchor 20 from proximally advancing into the tissue opening 22.

Figure 7:
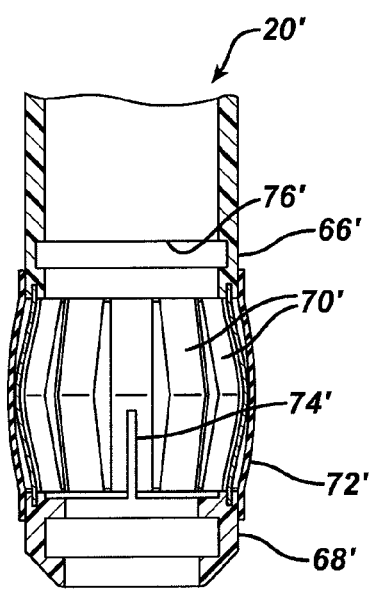
FIG. 7 is a side, cross-sectional view of another embodiment of an anchor including a plurality of wide flexible wires, the anchor being in an undeployed configuration.
Figure 8:
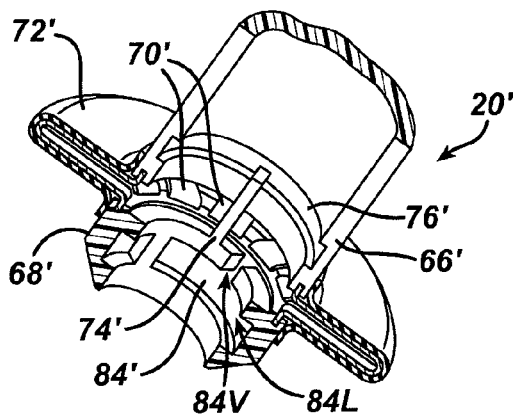
FIG. 8 is a perspective, cross-sectional view of the anchor of FIG. 7 in a deployed configuration.

FIGS. 7 and 8 illustrate another exemplary embodiment of an anchor 20' including a plurality of flexible wires 70' extending between proximal and distal rims 66', 68' of the anchor 20'. A flexible outer sheath 72' can be disposed around the wires 70'. The anchor 20' can generally be configured and used similar to other anchors discussed herein. However, in this illustrated embodiment, the wires 70' each extend substantially parallel to the longitudinal axis of the anchor 20' when the anchor is in an undeployed configuration, shown in FIG. 7. As shown in the illustrated embodiment, the anchor 20' can include one or more longitudinal posts or clips 74', generally referred to as "clips," that can extend proximally from the distal rim 68' of the anchor 20' and can be configured to engage a circumferential channel or groove 76', generally referred to as a "groove," formed in the proximal rim 66' of the anchor 20' to releasably lock the anchor 20' in a deployed configuration, shown in FIG. 7. In this way, a surgical tool such as an obturator can be configured to rotate the anchor 20' to move the anchor 20' between the deployed and undeployed configurations, and a surgical access device including the anchor 20' need not include a string configured to move the anchor 20' between the deployed and undeployed configurations. Various exemplary embodiments of anchors are described in more detail in U.S. patent application Ser. No. 12/636,174 entitled "Methods And Devices For Providing Access Through Tissue To A Surgical Site," filed Dec. 11, 2009 [Attorney Docket No. 100873-380 (END6634USNP)], U.S. patent application Ser. No. 12/636,184 entitled "Methods And Devices For Providing Access Through Tissue To A Surgical Site," filed Dec. 11, 2009 [Attorney Docket No. 100873-381 (END6634USNP1)], and U.S. patent application Ser. No. 12/636,191 entitled "Methods And Devices For Providing Access Through Tissue To A Surgical Site," filed Dec. 12, 2009 [Attorney Docket No. 100873-382 (END6634USNP2)], which are hereby incorporated by reference in their entireties.

The obturator 18 can also have a variety of sizes, shapes, and configurations. Exemplary embodiments of an obturator are described in more detail in previously mentioned U.S. patent application Ser. No. 12/636,174 entitled "Methods And Devices For Providing Access Through Tissue To A Surgical Site," filed Dec. 11, 2009 [Attorney Docket No. 100873-380 (END6634USNP)] U.S. patent application Ser. No. 12/636,184 entitled "Methods And Devices For Providing Access Through Tissue To A Surgical Site," filed Dec. 11, 2009 [Attorney Docket No. 100873-381 (END6634USNP1)], and U.S. patent application Ser. No. 12/636,191 entitled "Methods And Devices For Providing Access Through Tissue To A Surgical Site," filed Dec. 11, 2009 [Attorney Docket No. 100873-382 (END6634USNP2)], and in U.S. Pat. No. 6,017,356 entitled "Method For Using A Trocar For Penetration And Skin Incision", issued on Jan. 25, 2000, and U.S. Patent Publication No. 2007/0260273 entitled "Endoscopic Translumenal Surgical Systems," filed May 8, 2006, which are hereby incorporated by reference in their entireties.

Generally, the obturator 18 can include an elongate shaft 78 having a proximal end (not shown) including a handle (not shown) configured to be handheld outside a patient's body and a distal end with a tip 80 configured to be inserted through tissue. The obturator 18 in the illustrated embodiment is a hollow member with at least the shaft 78 being substantially flexible, but the obturator 18 can be substantially rigid and/or solid. The shaft 78 can be made substantially flexible using various techniques. For non-limiting example, the shaft 78 can be formed from a flexible material, and/or it can include one or more features formed therein to facilitate flexibility, such as a plurality of cut-outs or slots. In other embodiments, the shaft 78 can be formed from a plurality of linkages that are movably coupled to one another. The shaft 78 can also include regions that vary in flexibility. For non-limiting example, certain portions of the shaft 78, such as the distal portion, can be more rigid than other portions of the shaft 78, such as the proximal portion, to facilitate insertion of the obturator 18 through tissue alone or disposed within the cannula 14. Varying flexibility of the shaft 78 can be achieved in a variety of ways as will be appreciated by a person skilled in the art, such as by forming the shaft 78 from different materials, varying the diameter or thickness of the shaft 78, etc. The shaft 78 can also include other features to facilitate use, such as one or more spiral wires embedded therein and configured to preventing kinking of the shaft 78.

The size and shape of the shaft 78 can vary, but as shown in FIG. 1, the shaft 78 can have a longitudinal length greater than a longitudinal length 14L of the cannula 14 such that the obturator 18 can be inserted through the cannula's working channel 16 with the shaft's proximal end located proximal to the cannula's proximal end 14p and the distal tip 80 located distal to the anchor 20. The obturator's handle can have a maximum diameter greater than a diameter of at least a proximal-most end of the working channel 16, e.g., greater than the segment's proximal inner diameter D1, thereby preventing the obturator 18 from being fully inserted into the cannula 14 through the proximal end 14p thereof.

The obturator's distal tip 80 can also have a variety of shapes, sizes, and configurations. Generally, the tip 80 can be configured to penetrate tissue. The tip 80 can be composed of any one or more flexible and/or rigid materials, although the tip 80 in the illustrated embodiment is rigid, e.g., composed of stainless steel, titanium, etc., to help the tip 80 penetrate tissue. In an exemplary embodiment, the tip 80 can be transparent to allow visualization therethrough. For non-limiting example, an endoscope (not shown) can be proximally inserted into the obturator 18 and be disposed within the obturator 18 to provide visualization through the obturator's clear distal tip 80. The tip 80 can be integrally formed with a reminder of the shaft 78, or it and/or the tip 80 can be removably or fixedly attached to the shaft 78, e.g., using an interference fit, an adhesive, ultrasonic welding, etc. The tip 80 can have a variety of shapes, e.g., conical (as shown in FIG. 1), triangular, rectangular, rounded, etc. The tip 80 can include one or more features to help it penetrate tissue, e.g., a tapered shape, a beveled edge (including a chamfered edge), a pointed needle, an electronic cutter, a sharp cutting blade, etc. Various exemplary configurations for the tip 80 are described in more detail in previously mentioned U.S. Patent Publication No. 2007/0260273 entitled "Endoscopic Translumenal Surgical Systems," filed May 8, 2006.

Figure 6:
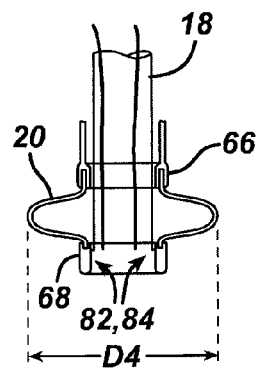
FIG. 6 is a side, cross-sectional view of the anchor and the obturator of FIG. 5 with the anchor in a deployed configuration.

The distal end of the obturator 18 can also be configured to engage the anchor 20 to facilitate deployment of the anchor 20. As illustrated in FIGS. 5 and 6, the obturator 18 and the anchor 20 can be configured to be keyed together with the obturator 18 and the anchor 20 including an engagement and release mechanism to key to each other. The engagement and release mechanism can include a bayonet latch mechanism. At least one bayonet foot or pin, e.g., a plurality of radially arranged bayonet feet or pins 82 spaced equidistantly or any other distance apart, can extend any length from an inner perimeter of the anchor 20, e.g., from an inner sidewall of the distal rim 68, and the pins 82 can be configured to engage corresponding slots 84 formed in an outer circumferential surface of the obturator 18. The slots 84 can have any shape and size and can be the same as or different from any other of the slots 84. As discussed further below, the slots 84 can each include a vertically-extending portion in which the pins 82 can be distally inserted and a laterally-extending portion in which the pins 82 can laterally slide. The pins 82 can have any shape and size and can be the same as or different from any other of the pins 82. The pins 82 can be configured to be inserted into the vertically-extending portion of the slots 84 and if identical, as in the illustrated embodiment, can be interchangeably inserted into any of the slots 84. In another exemplary embodiment, an obturator can include pins configured to engage slots formed in an anchor. For non-limiting example, in the embodiment illustrated in FIGS. 7 and 8, the anchor 20' includes slots 84' each having a vertically-extending portion 84v in which a pin extending from a surgical tool (not shown) can be proximally inserted and a laterally-extending portion 84L in which the pin can laterally slide. Exemplary embodiments of bayonet latch mechanisms and other engagement and release features are described in more detail in U.S. patent application Ser. No. 12/399,482 entitled "Methods and Devices for Providing Access to a Body Cavity" filed on Mar. 6, 2009, and U.S. patent application Ser. No. 12/512,542 entitled "Methods and Devices for Providing Access Into a Body Cavity" filed on Jul. 30, 2009, which are hereby incorporated by reference in their entireties.

The obturator 18 can also be configured to rotate about a longitudinal axis of the obturator 18, which is the same as the longitudinal axis A in the illustrated embodiment in FIG. 1, when the obturator 18 is disposed therein, to deploy the anchor 20, as discussed further below.

In use, referring again to FIG. 1, the plurality of segments 34 defining the cannula 14 can have the obturator 18 disposed therein such that the obturator's distal tip 80 extends distally beyond the anchor 20. The cannula 14 and the obturator 18 can be inserted through the opening 24 in the tissue 22 with the obturator's tip 80 penetrating the tissue 22 to ease insertion of the cannula 14 and obturator 18 therethrough. When the cannula 14 is inserted through the tissue 24, the anchor 20 can be in the first configuration having the smaller diameter D3, as shown in FIGS. 1 and 5, which can ease insertion of the anchor 20 through the tissue 24. The cannula 14 and the obturator 18 can be inserted through the tissue 24 until at least the anchor 20 is disposed within the body cavity 26, as shown in FIG. 1. With the anchor 20 positioned in the body cavity 26, the anchor 20 can be moved from the first configuration to the second configuration, e.g., the anchor 20 can be deployed. In this way, the anchor 20 can expand to engage the distal surface 24d of the tissue 24 facing the body cavity 26 with the cannula 14 extending through the tissue opening 22. Because the deployed anchor 20 with the second outer diameter D4 can be larger than the cannula's maximum outer diameter, the anchor 20 can be prevented from being drawn proximally into the tissue opening 22 having substantially the same diameter as the cannula's maximum outer diameter.

The anchor 20 can be moved between the first and second configurations in a variety of ways. As mentioned above, in an exemplary embodiment, the obturator 18 can be configured to move the anchor 20 between the first and second configurations. With the obturator 18 disposed in the working channel 16 and having the anchor 20 keyed thereto through engagement of the bayonet pins 82 and the slots 84, the obturator 18 can be rotated in a first direction, e.g., a clockwise direction, relative to the anchor 20, thereby causing the bayonet pins 82 to travel laterally within the slots 84, e.g., within the laterally-extending portion of the slots 84 away from the vertically-extending portion of the slots 84, to a position in which the pins 82 abut terminal ends of the slots 84, thereby locking the obturator 18 to the anchor 20. One or more of the slots 84 can angle proximally or distally at their respective terminal ends such that the bayonet pins 82 can proximally or distally slide and snap into the terminal ends to help ensure that the bayonet pins 82 fully slide through the slots 84 to lock the obturator 18 to the anchor 20. The laterally-extending portions of the slots 84 can extend in both directions from the vertically-extending portions of the slots 84 to allow the bayonet pins 82 to move either clockwise or counterclockwise to lock the obturator 18 to the anchor 20. In some embodiments, the laterally-extending portions of the slots 84 can extend in only one direction from the vertically-extending portions of the slots 84.

With the obturator 18 locked to the anchor 20, e.g., with the bayonet pins 82 misaligned from the vertically-extending portion of the slots 84, the obturator 18 can be pulled proximally relative to the segments 34, as shown in FIG. 6, thereby pulling the distal rim 68 of the anchor 20 toward the proximal rim 66 and expanding the wires 70 radially outward to change the anchor's shape. The obturator 18 can be optionally rotated about the working channel's axis A when the obturator 18 is pulled proximally, which can help deploy and flare the anchor 20. In an embodiment in which the distal anchor includes clips, pulling the obturator 18 in a proximal direction also proximally moves the clips attached to the anchor's distal rim, thereby allowing the clips to engage the groove formed in the anchor's proximal rim to lock the rims together and lock the anchor in the deployed configuration. The anchor 20 can be locked in the deployed, second configuration before or after the obturator 18 is removed from the working channel 16.

Figure 9:
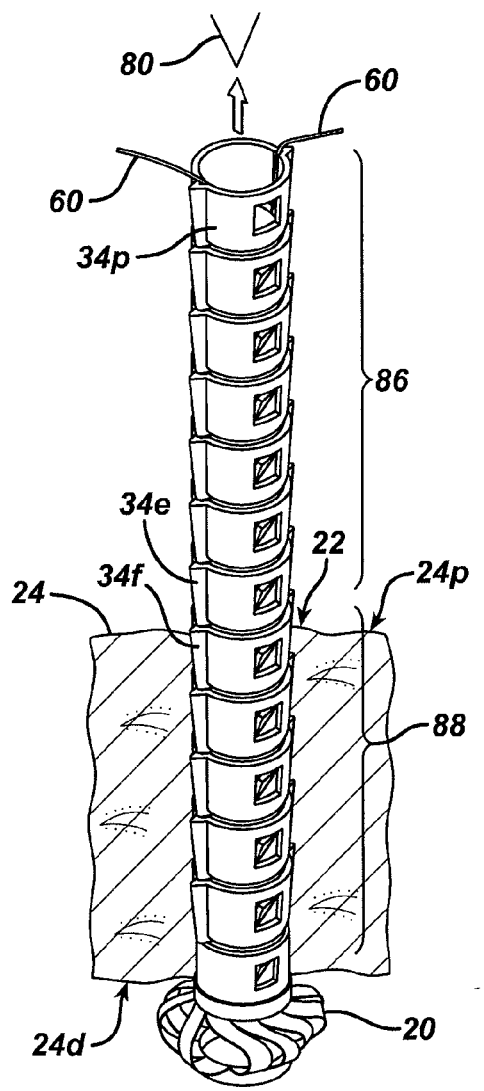
FIG. 9 is a perspective, partial cross-sectional view of the surgical access device of FIG. 1 with the anchor in a deployed configuration and the obturator being removed from the cannula.

The obturator 18 can be removed from the device 10 by rotating the obturator 18 about the obturator's longitudinal axis and the working channel's longitudinal axis A to laterally move the bayonet pins 82 within the slots 84 until the bayonet pins 82 axially align with the vertically-extending portion of the slots 84, at which point the obturator 18 can be pulled proximally to disengage the bayonet pins 82 from the slots 84 and allow removal of the obturator 18 from the cannula 14, as shown in FIG. 9.

As mentioned above, the strings 60 can be attached to the anchor 20, e.g., to the anchor's distal rim 68, and can be configured to lock the anchor 20 in the deployed configuration, such as through mating engagement with at least one of the segments 34. When the cannula 14 and obturator 18 are inserted through the tissue 24, the strings 60 can extend through the working channel 16 between an inner wall of the cannula 14 and an outer wall of the obturator 18, as shown in FIG. 1. Following deployment of the anchor 20, the strings 60 can be manipulated to move within the longitudinal channels 62 to be held therein, as shown in FIG. 9. As shown, each channel's outward triangular tip can be configured to pinch its respective one of the strings 60 to securely hold them therein. The strings 60 can be pulled into the channels 62 and be pinched by any of the segments 34 to be held therein, but in the illustrated embodiment in FIG. 9, the strings 60 are only pinched by a proximal-most one of the segments 34p.

Figure 10:
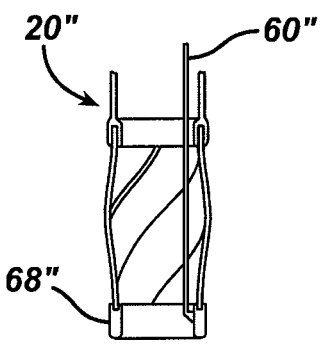
FIG. 10 is a side, cross-sectional view of another embodiment of an anchor including a plurality of wide flexible wires, the anchor being in an undeployed configuration and having a pull string received therein.

Before the strings 60 are locked to the cannula 14, one or more of the strings 60 can be optionally pulled in a proximal direction to encourage full deployment of the anchor 20, e.g., by pulling the anchor's distal rim 68 toward the anchor's proximal rim 66 such that the anchor's mid-portion more fully flares. In another exemplary embodiment, shown in FIGS. 10 and 11, an anchor 20" can be deployed by proximally pulling at least one string 60" attached to the anchor 20", e.g., to the anchor's distal rim 68", to move the anchor 20" from a first, undeployed configuration, shown in FIG. 10, to a second, deployed configuration, shown in FIG. 11. In this way, an obturator need not be keyed to the anchor 20 to facilitate the anchor's deployment.

Referring again to FIG. 9, with the anchor 20 in the second configuration, the cannula 14 can be moved in a proximal direction relative to the tissue 24 such that the flared mid-portion of the anchor 20 can contact the distal surface 24d of the tissue 24. With the anchor 20 so contacting the tissue's distal surface 24d, the cannula 14 can be positioned with a proximal, exposed portion 86 extending proximally above the tissue's proximal surface 24p and a distal, inserted portion 88 positioned within the tissue opening 22 between the proximal and distal surfaces 24p, 24d of the tissue 24. The exposed portion 86 can include at least the proximal-most segment 34p, and the inserted portion 88 can include at least the distal-most segment 34d. The inserted portion 88 can include at least one segment 34 which is only partially disposed within the tissue opening 22, e.g., with a proximal portion extending above the tissue's proximal surface 24p, to facilitate handling of the cannula 14. Such a position of the cannula 14 can mimic or simulate the cannula's position within the tissue opening 22 when the tissue 24 is compressed between the anchor 20 in the second configuration and a housing (not shown) disposed around the cannula 14 and abutting the tissue's proximal surface 24p. Thus, the exposed portion 86 of the cannula 14 can indicate a portion of the cannula 14 which is unnecessary to extend the cannula 14 through the tissue 24 and thus a portion of the cannula 14 that can be removed to shorten the cannula's longitudinal length 14L and thereby better approximate a longitudinal length of the tissue opening 22 in which the device 10 is disposed.

Figure 12:
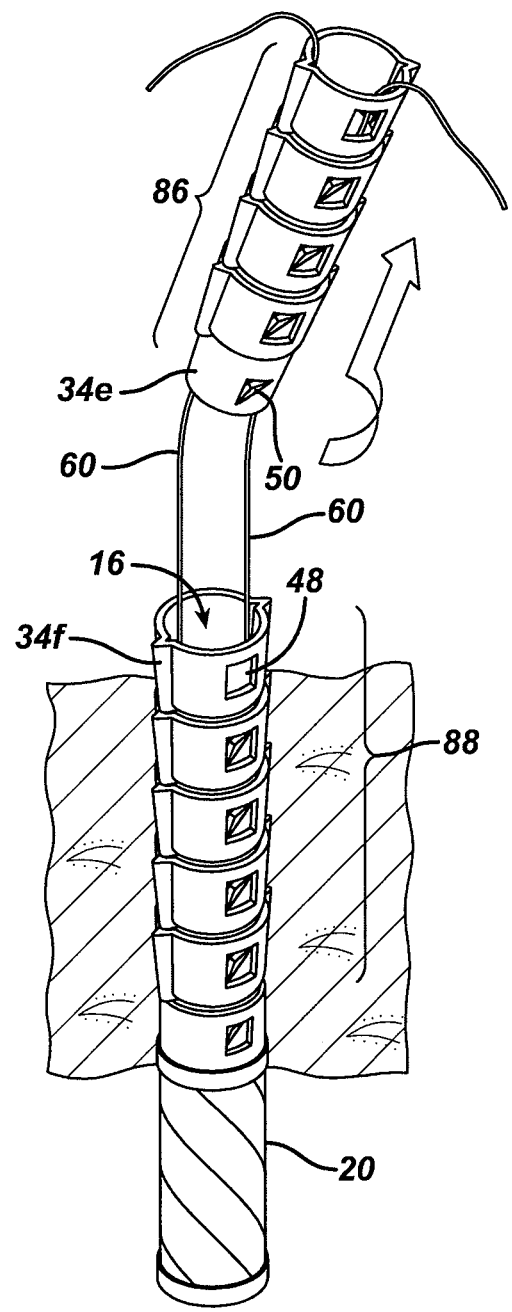
FIG. 12 is a perspective, partial cross-sectional view of the surgical access device of FIG. 9 with the anchor in an undeployed configuration and a proximal portion of the cannula being removed from a distal remainder of the cannula positioned within the tissue opening.

The exposed portion 86 of the cannula 14 can be removed from the inserted portion 88 of the cannula 14 in a variety of ways. As shown in FIG. 12, the cannula's exposed portion 86 can be rotated relative to the cannula's inserted portion 88 to separate the cannula 14 at a junction of the exposed and inserted portions 86, 88. In other words, the tab 50 of the distal-most segment 34e in the exposed portion 86 can be disengaged from the window 48 of the proximal-most segment 34f in the inserted portion 88 to allow the exposed portion 86 to be removed from the surgical area. The inserted portion 88 of the cannula 14 can be held in position by hand and/or with a surgical instrument to prevent its rotation when the exposed portion 86 is rotated to disengage the tab 50. The ribs 58 can also be configured as an anti-rotation feature with the tissue contacting the ribs 58 of the segments 34 forming the inserted portion 88 of the cannula 14 and providing resistance thereto to substantially prevent rotation of the inserted portion 88 of the cannula 14. Any or all of the segments 34 forming the removed exposed portion 86, and/or any other modular segments 34, can be reattached to the distal portion 88 at any time during a surgical procedure.

In one exemplary embodiment, a surgical instrument in the form of a collar can be disposed around the cannula 14 to facilitate removal of the exposed portion 86 from the inserted portion 88. The collar can have a variety of sizes, shapes, and configurations. The collar can be composed of any one or more flexible and/or rigid materials, although the collar in the illustrated embodiment of FIG. 13 is rigid. In one exemplary embodiment illustrated in FIG. 13, a cannula 114 including a plurality of removably coupled segments 134 can be configured and used similar to the cannula 14 of FIG. 1 and can be positioned within an opening 122 in tissue 124. A collar 190 having a bore extending therethrough can be slidably disposed around the cannula 114, either after or before the cannula 114 has been positioned within the tissue opening 122, and the collar 190 can be positioned relative to the cannula 114 extending through the collar's bore such that a distal surface 190d of the collar 190 abuts a proximal surface 124p of the tissue 124. In this way, the collar 190 can engage a selected one of the plurality of segments 134a, e.g., a proximal-most segment of an inserted portion of the cannula 114, with at least one other segment 134 extending proximally therefrom, e.g., an exposed portion of the cannula 114. In other words, the collar 190 can be configured to slide along the cannula 114 to selectively engage one of the cannula's segments 134. As mentioned above, the segments 134 can each include at least one longitudinal rib 158, which can be configured as an alignment feature configured to align the collar 190 relative thereto, e.g., by including channels (not shown) configured to slidably receive the ribs 158 therein. In this way, the collar 190 can be slid along the cannula 114 in at least one predetermined position, which can facilitate assembly of the surgical access device.

As mentioned above, to release a proximal portion of the cannula 114 from a distal portion of the cannula 114, e.g., to remove the exposed portion of the cannula 114, the proximal portion can be rotated relative to the distal portion. As also mentioned above, the segments 134 can each include at least one longitudinal rib 158, which can be configured as an anti-rotation feature. The collar 190 can be configured to engage the longitudinal ribs 158 of the selected one of the segments 134a such that the selected one of the segments 134 and the segments 134 extending distally therefrom with an anchor 120 coupled to a distal-most one of the segments 134 can be prevented from rotating when the one or more segments 134 proximal to the collar 190 are rotated. A person skilled in the art will appreciate that while the collar 190 in the illustrated embodiment engages only one of the segments 134a, the collar 190 and/or the segments 134 can have a shape and size such that the collar 190 can be configured to concurrently selectively engage more than one of the segments 134. If the collar 190 simultaneously engages more than one of the segments 134, e.g., such that the ribs 158 of the multiple segments are seated in channels of the collar 190, then each of the segments 134 proximal to a proximal-most one of the engaged segments 134 can be rotated relative to a remainder of the segments 134 to be disconnected therefrom. A person skilled in the art will also appreciate that while all of the segments 134 proximal to a proximal-most one of the engaged segments 134 can be rotated as a singular unit relative to a remainder of the segments 134 to be disconnected therefrom as a singular unit, the proximal-most one of the segments 134 can be rotated alone or together with any one or more of the other segments 134 proximal to a proximal-most one of the engaged segments 134 to remove part of the proximal portion from the remainder of segments. In other words, segments 134 can be configured to be selectively removed individually and/or in groups of two or more.

Referring again to FIG. 12, before or after the exposed portion 86 is disconnected from the inserted portion 88 such that the cannula 114 is separated into multiple cannulated tubular members, the strings 60 can be disengaged from the channels 62 in the exposed portion 86 to allow the exposed portion 86 to be safely removed from the surgical area. Such disengagement of the strings 60 can move the anchor 20 from the second configuration to the first configuration, as shown in FIG. 12, with the strings 60 being loose within the working channel 16 of the cannula 14. Optionally, an excess length of the strings 60 can be trimmed proximal to the inserted portion 88, e.g., proximal to the segment 34f.

As mentioned above, a housing can be positioned at a proximal end of the cannula 14 positioned in the tissue opening 22. A collar can facilitate attachment of a housing to the cannula 14, although a person skilled in the art will appreciate that a housing can be attached to the cannula 14 without a collar. In one exemplary embodiment, shown in FIGS. 14-16, a collar 90 can be slidably disposed around the cannula 14 to facilitate attachment of a housing 12 thereto.

The housing 12 can have a variety of sizes, shapes, and configurations. Generally, the housing 12 can be configured to provide a pathway for receiving a surgical instrument such the obturator 18, an endoscope, a retractor, a dissector, a cutting instrument, etc. Exemplary housing configurations are described in more detail in U.S. Pat. No. 6,017,356 entitled "Method For Using A Trocar For Penetration And Skin Incision", issued on Jan. 25, 2000, U.S. Patent Publication No. 2004/0230161 entitled "Trocar Seal Assembly," filed on Mar. 31, 2004, U.S. Patent Publication No. 2007/0185453 entitled "Conical Trocar Seal," filed on Oct. 15, 2003, U.S. patent application Ser. No. 12/636,174 entitled "Methods And Devices For Providing Access Through Tissue To A Surgical Site," filed Dec. 11, 2009 [Attorney Docket No. 100873-380 (END6634USNP)], U.S. patent application Ser. No. 12/636,184 entitled "Methods And Devices For Providing Access Through Tissue To A Surgical Site," filed Dec. 11, 2009 [Attorney Docket No. 100873-381 (END6634USNP1)], and U.S. patent application Ser. No. 12/636,191 entitled "Methods And Devices For Providing Access Through Tissue To A Surgical Site," filed Dec. 11, 2009 [Attorney Docket No. 100873-382 (END6634USNP2)], which are hereby incorporated by reference in their entireties.

The housing 12 can include at least one sealing element configured to provide at least one of a channel seal and an instrument seal. A person skilled in the art will appreciate that the device 10 can include any number of sealing elements and that in addition or in alternative to at least one sealing element in the housing 12, the cannula 14 can include one or more sealing elements. The sealing element can have a variety of sizes, shapes, and configurations. In one exemplary embodiment, the housing 12 can include a distal sealing element (not shown) that includes a duckbill seal that provides a channel seal, and a proximal sealing element that can include a septum seal 15 that provides an instrument seal. In use, when a surgical instrument is passed through the proximal sealing element, the proximal sealing element can engage and form a seal around an outer surface of the instrument to thereby prevent passage of fluids and gas through the proximal sealing element. When no instrument is disposed therethrough, the proximal sealing element will generally not form a seal in the working channel 16. Exemplary instrument seal configurations are described in more detail in U.S. patent application Ser. No. 12/399,482 entitled "Methods And Devices For Providing Access Into A Body Cavity," filed Mar. 6, 2009, U.S. Patent Publication No. 2004/0230161 entitled "Trocar Seal Assembly," filed on Mar. 31, 2004, U.S. Patent Publication No. 2007/0185453 entitled "Conical Trocar Seal," filed on Oct. 15, 2003, U.S. patent application Ser. No. 12/636,174 entitled "Methods And Devices For Providing Access Through Tissue To A Surgical Site," filed Dec. 11, 2009 [Attorney Docket No. 100873-380 (END6634USNP)], U.S. patent application Ser. No. 12/636,184 entitled "Methods And Devices For Providing Access Through Tissue To A Surgical Site," filed dec. 11, 2009 [Attorney Docket No. 100873-381 (END6634USNP1)], and U.S. patent application Ser. No. 12/636,191 entitled "Methods And Devices For Providing Access Through Tissue To A Surgical Site," filed Dec. 11, 2009 [Attorney Docket No. 100873-382 (END6634USNP2)], which are hereby incorporated by reference in their entireties.

When the instrument is further inserted through the distal sealing element, the instrument can open the distal sealing element and pass into the cannula 14. A person skilled in the art will appreciate that while any channel or zero-closure seal can be used for the distal sealing element, e.g., a duckbill seal, cone seal, flapper valve, gel seal, diaphragm seal, lip seal, iris seal, a non-linear sealing element such as a sealing element with an S-shaped opening, etc., can be used. Generally, a zero-closure seal can be configured to form a seal in a working channel when no instrument is disposed therethrough to thus prevent the leakage of insufflation gases delivered through the surgical access device to the body cavity. A duckbill seal can generally have opposed flaps that extend at an angle toward one another in a distal direction and that come together at a distal end to form a seal face. The opposed flaps can be movable relative to one another to allow the seal face to move between a closed position, in which no instrument is disposed therethrough and the seal face seals the working channel of the surgical access device, and an open position in which an instrument is disposed therethrough. A duckbill seal can include various other features, as described in more detail in U.S. Patent Publication No. 2009/0005799 entitled "Duckbill Seal with Fluid Drainage Feature," filed on Jun. 29, 2007, which is hereby incorporated by reference in its entirety. In addition, the seal face of the duckbill seal can be in any nonlinear shape or configuration known in the art, for example in an S-shaped configuration, as described in more detail in U.S. Pat. No. 5,330,437, entitled "Self Sealing Flexible Elastomeric Valve and Trocar Assembly for Incorporating Same," filed Nov. 12, 1993, which is hereby incorporated by reference in its entirety.

The housing 12 can include an insufflation port 13 extending from a sidewall of the housing 12, although a person skilled in the art will appreciate that the insufflation port 13 can be located elsewhere in the housing 12 or in other locations. A person skilled in the art will also appreciate that the device 10 can include any number of insufflation ports and that an insufflation port can have a variety of configurations. Generally, the insufflation port 13 can be configured to pass an insufflation fluid through a flexible insufflation tube and into an insufflation orifice of the insufflation port 13 where the fluid can flow through the working channel 16 and into a body cavity. A stopcock can control fluid flow through the insufflation tube. In an exemplary embodiment, a surgical access device kit can include multiple modular stopcocks, e.g., an insufflation/vent three-way version, a twist to activate version, a spring loaded version, etc.

In the illustrated embodiment in FIG. 14, the collar 90 includes two releasably coupled c-shaped retainers 90a, 90b configured to snap or otherwise mate together to form the collar 90 positioned around the cannula 14. A person skilled in the art will appreciate that the retainers 90a, 90b can have any size and shape and that the collar 90 can include a singular member or a member including two or more attachable retainers. Each of the retainers 90a, 90b includes an inner raised portion 92a, 92b configured to form a valve assembly ring 92 when the retainers 90a, 90b are attached together, as shown in FIG. 14. The valve assembly ring 92 can be configured to attach to the housing 12 in any way, e.g., by snap fit, by threading, etc. Although the collar 90 in the illustrated embodiment is coupled to the cannula 14 after the cannula 14 has had one or more segments 34 removed therefrom to adjust the cannula's longitudinal length 14L, as mentioned above the collar 90 can be coupled to the cannula 14 before any segments 34 are removed therefrom.

Figure 15:
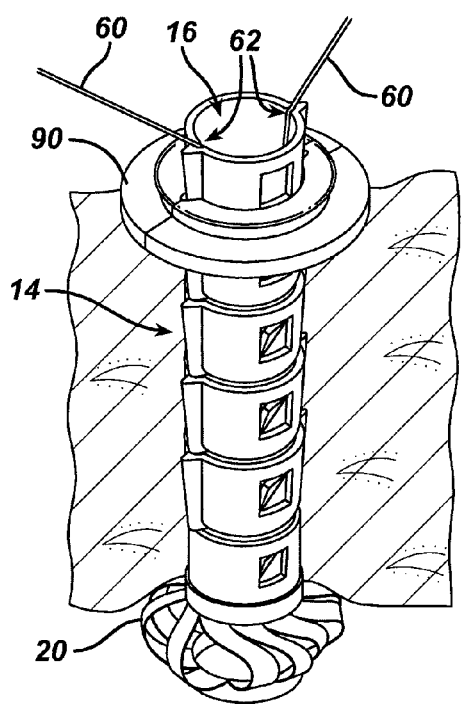
FIG. 15 is a perspective, partially cross-sectional view of the surgical access device of FIG. 14 with the anchor in a deployed configuration and with pull strings extending through the distal remainder of the cannula locking the anchor in the deployed configuration.
Figure 16:
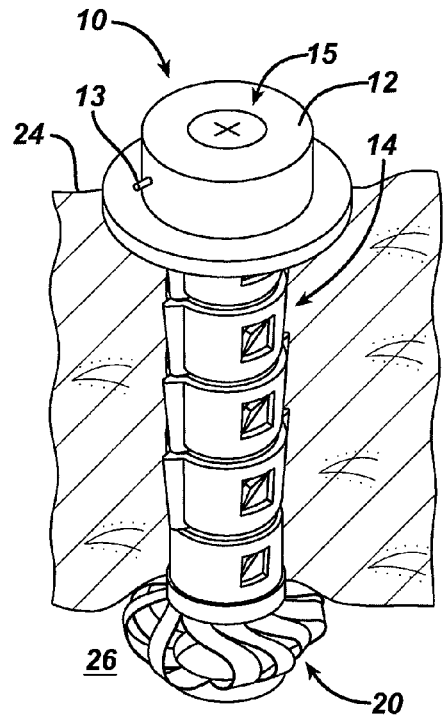
FIG. 16 is a perspective, partially cross-sectional view of the surgical access device of FIG. 15 with a proximal housing attached to the collar and the distal remainder of the cannula.

If the anchor 20 is in the first configuration with the collar 90 attached to the cannula 14 as shown in FIG. 14, the anchor 20 can be moved to the second configuration, e.g., by pulling the strings 60 as shown in FIG. 15. The strings 60 can be locked in the channels 62 as discussed above to lock the anchor 20 in the second configuration. As also discussed above, excess lengths of the strings 60 can optionally be trimmed before and/or after attachment of the housing 12 to the collar 90 to reduce interference of the strings 60 with the housing 12. In an exemplary embodiment, the strings 60 have sufficient length such that they can extend from within the working channel 16 and be secured between the collar 90 and the housing 12 when the housing 12 is attached to the collar 90, as shown in FIG. 16, to help ensure that the anchor 20 is locked in the deployed configuration. With the device 10 assembled and positioned in the tissue opening 22 as shown in FIG. 16 such that the tissue 24 is compressed between the anchor 20 and the collar 90 and housing 12, one or more surgical instruments (not shown) can be inserted therethrough to perform a surgical procedure in the body cavity 26.

The device 10 can be removed from the tissue opening 22 in a way similar to its positioning therein. The housing 12 can be removed from the collar 90, e.g., unsnapped, unscrewed, etc. therefrom, which can expose the strings 60 positioned between the housing 12 and the collar 90. The strings 60 can be removed from the channels 62 in which they are secured, thereby allowing the anchor 20 to move from the second configuration to the first configuration. The collar 90 and/or the cannula 14 can then be grasped and pulled in a proximal direction to remove the cannula 14 and the anchor 20, in the undeployed configuration, from the tissue 24. The collar 90 can optionally be removed from the cannula 14 before the cannula 14 is removed from the tissue opening 22.

Figure 17:
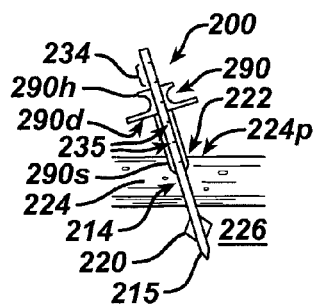
FIG. 17 is a side, cross-sectional view of another embodiment of a surgical access device including a cannula positioned within a tissue opening, having a collar disposed therearound proximal to the tissue opening and partially inserted into the tissue opening, and having an anchor in an deployed configuration at a distal end thereof.

The devices of FIGS. 1-16 include devices configured to adjust in longitudinal length through removal and/or addition of one or more modular segments forming a cannula. In another exemplary embodiment, a surgical access device can include a cannula configured to adjust in longitudinal length through breaking off a portion of the cannula. In one embodiment, illustrated in FIGS. 17-20, a surgical access device 200 can include a collar 290 slidably disposed around a cannula 214 and be generally configured and used similar to other devices disclosed herein. The device 200 can also include a housing 212 from which the cannula 14 distally extends. The cannula 214 in the embodiment of FIG. 17 includes an elongate tubular member having a plurality of separable segments 234 configured to be removed one or more at a time from the cannula 214. The segments 234 can be removed one or more at a time from a proximal end and/or a distal end of the cannula 214, but as discussed further below, in an exemplary embodiment, one or more segments 234 can be removed from the cannula's proximal end. The segments 234 can be removable from the cannula 214 by breaking the cannula 214 at one or more scored or otherwise weakened regions 235, generally referred to as "weakened regions," at discrete locations along a longitudinal length of the cannula 214. The weakened regions 235 can be spaced axially along the cannula 214 such that each of the segments 234 has substantially the same longitudinal length, as shown in FIG. 17, or such that any one or more of the segments 234 differs in longitudinal length from any one or more of the other segments 234.

In use, the cannula 214 can be inserted through an opening 222 in tissue 224 similar to other cannulas discussed herein. The cannula 214 can have a penetrating tip 215 located distal to an anchor 220 at a distal end of the cannula 214 and configured to help insert the cannula 214 through the tissue 224, and/or as discussed above, the cannula 214 can have a surgical instrument such as an obturator inserted therethrough to assist in inserting the cannula 214 through the tissue 224. The anchor 220 can be deployed within a body cavity 226 underlying the tissue 224, similar to other anchors discussed herein.

Figure 18:
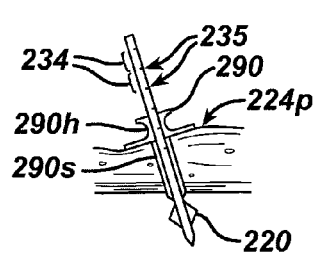
FIG. 18 is a side, cross-sectional view of the surgical access device of FIG. 17 with the collar distally advanced around the cannula such that tissue is compressed between the collar and the anchor.

The collar 290 can be positioned around the cannula 214 before or after the cannula 214 is positioned within the tissue opening 222. As shown in FIGS. 17 and 18, the collar 290 can be slid distally along the cannula 214 until an elongate tubular sleeve 290s of the collar 290 extending distally from a head 290h of the collar 290 is positioned within the tissue opening 222 and a distal surface 290d of the head 290h abuts a proximal surface 224p of the tissue 224 and the tissue 224 is compressed between the collar head 290h and the anchor 220. The collar sleeve 290s can be configured to provide additional stability to the cannula 214 and to help prevent weakened portions 235 positioned within the tissue opening 222 from breaking the cannula 214 when positioned therein.

Figure 19:
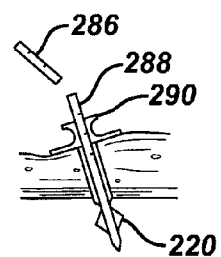
FIG. 19 is a side, cross-sectional view of the surgical access device of FIG. 18 with a proximal portion of the cannula being broken from a distal remainder of the cannula positioned within the tissue opening.

With the tissue 224 compressed between the collar 290 and the anchor 220, a proximal, exposed portion 286 of the cannula 214 can be positioned proximally above the collar 290 and a distal, inserted portion 288 can be disposed within the collar 290 and/or extend distally from the collar 290. The exposed portion 286 of the cannula 214 can be removed from the proximal end of the cannula 214 as shown in FIG. 19 by breaking the cannula 214 at a selected one of the weakened regions 235, e.g., at any one of the weakened regions 235 located proximal to the collar 290. The cannula 214 can be broken by hand and/or with assistance of a surgical instrument. A person skilled in the art will appreciate that the cannula 214 can be shortened multiple times by breaking the cannula 214 at multiple ones of the weakened regions 235.

The housing 212 can be attached to the collar 290, e.g., by snap fit, as shown in FIG. 20, such that one or more surgical instruments (not shown) can be inserted through the device 200 and into the body cavity 226. Although the housing 212 in the illustrated embodiment is attached to the collar 290 after the cannula 214 has been adjusted to a desired longitudinal length, the housing 220 can be mated to the collar 290 at any time, including before the collar 290 is slidably mated to the cannula 214. In some embodiments, the device 200 need not include the collar 290. The device 200 can be disassembled and removed from the tissue 224 similar to that discussed above.

The devices of FIGS. 1-20 can be configured to adjust in longitudinal length through removal and/or addition of segments of the cannula. In another exemplary embodiment, a surgical access device having a cannula distally extending from a housing can be configured to adjust in longitudinal length by the housing being configured to cut the cannula. Generally, the cannula having a first longitudinal length can be positioned in a tissue opening with the housing located outside the patient's body on one side of the tissue and a distal end of the cannula being located in a body cavity underlying the tissue. The housing can be configured to change the cannula's longitudinal length from the first longitudinal length to a second, shorter longitudinal length before and/or after the cannula is positioned in the tissue opening. In this way, the cannula can be adjusted to more closely approximate the tissue's thickness and to allow the device to be more securely positioned within the tissue.

In an exemplary embodiment illustrated in FIG. 21, a surgical access device 300 can include a housing 312 having a cannula 314 distally extending therefrom. However, the housing 312 in the illustrated embodiment of FIG. 21 can be configured to cut the cannula 314 to reduce the cannula's longitudinal length. The device 300 can also include a collar 390 fixedly or removably attached to a proximal portion of the housing 312, and/or an anchor (not shown) at a distal end of the cannula 314. The housing 312, the collar 390, and the cannula 314 can each have a variety of sizes, shapes, and configurations, and the device 300 can be generally configured and used similar to other like-named elements discussed herein. As shown in FIG. 21, the cannula 314 can include an elongate tubular member having a proximal, threaded portion 314p with an external thread 313 and having a distal, unthreaded portion 314d, although the cannula's distal portion 314d can also be threaded. The cannula's threads 313 can be configured to engage corresponding threads 311 within a fluid-tight interior cavity 309 of the housing 312 such that the cannula 313 can threadably move relative to the housing 312. Although the device 300 can include any number of seals located anywhere in the device 300, in an exemplary embodiment, the cannula 314 can include at least one of a channel seal and an instrument seal within its distal portion 314d.

Optionally, a protective sleeve can be disposed over an external surface of the cannula 314, or any other cannula disclosed herein. The sleeve can have a variety of sizes, shapes, and configurations, but can include a fluid-impermeable flexible member disposed over an external surface of the cannula 314 to facilitate sealing of the cannula 314 and facilitate insertion and removal of the cannula 314 from tissue. The sleeve can be adhered to an external surface of the cannula 314 in any number of ways, e.g., through a tight cling fit. The sleeve can optionally be positioned within a tissue opening separately from the cannula 314, and the cannula 314 can be inserted into the sleeve already positioned in the tissue opening. The sleeve can be configured to move with the cannula 314 relative to the housing 312 and be cut with the cannula 314. In some embodiments, the sleeve can be located distal to the housing 312 and be configured to collapse, fold, or bunch, e.g., be in the form of as a bellows, when the cannula 314 moves relative to the housing 312. In this way, the cannula 314 can be configured to be cut by the housing 312 without the sleeve being similarly cut but with the sleeve being configured to adjust in longitudinal length to complement the length of the cannula 314. The sleeve can be a continuous member extending along the cannula 314, or the sleeve can include a plurality of discrete members. Exemplary embodiments of protective sleeves are described in more detail in previously mentioned U.S. patent application Ser. No. 12/636,174 entitled "Methods And Devices For Providing Access Through Tissue To A Surgical Site," filed Dec. 11, 2009[Attorney Docket No. 100873-380 (END6634USNP)], U.S. patent application Ser. No. 12/636,184 entitled "Methods And Devices For Providing Access Through Tissue To A Surgical Site," filed Dec. 11, 2009 [Attorney Docket No. 100873-381 (END6634USNP1)], and U.S. patent application Ser. No. 12/636,191 entitled "Methods And Devices For Providing Access Through Tissue To A Surgical Site," filed Dec. 11, 2009 [Attorney Docket No. 100873-382 (END6634USNP2)].

The housing 312 can include a first rotatable knob 307 and a second rotatable knob 305, with each of the knobs 305, 307 being rotatable relative to one another about a longitudinal axis A2 of the device 300. The first and second knobs 307, 305 each include substantially circular rings with the first knob 307 being located distal to the second knob 305, but as will be appreciated by a person skilled in the art, the knobs 305, 307 can have any size, shape, and configuration. One or both of the knobs 305, 307 can optionally include a gripping feature such as indented portions 303 spaced around a perimeter or circumference of the knobs 305, 307 and configured to facilitate a hand or instrument hold of the knobs 305, 307.

The first knob 307 can be configured to rotate about the device's axis A2 to move the cannula 314 relative to the housing 312. A person skilled in the art will appreciate that while in the illustrated embodiment the first knob 307 threadably moves the cannula 314, any mechanism can be used to move the cannula 314 relative to the housing 312, such as a ratchet mechanism. The first knob 307 can be configured to rotate in a first direction, e.g., clockwise, to threadably move the cannula 314 in a proximal direction to shorten a longitudinal length of the cannula 314 extending distally from the housing 312, and be configured to rotate in a second, opposite direction, e.g., counterclockwise, to threadably move the cannula 314 in a distal direction to increase a longitudinal length of the cannula 314 extending distally from the housing 312. In this way, the cannula's longitudinal length distal to the housing 312 can be selectively adjusted to a desired length.

The second knob 305 can be configured to rotate about the device's axis A2 to rotate first and second actuators 321 relative to the cannula 314 to cut the cannula 314. Although the device 300 includes two actuators spaced equidistantly around a perimeter of the second knob 305, e.g., 180° degrees apart, the device 300 can include any number of actuators. The actuators can have a variety of sizes, shapes, and configurations. Generally, the actuators can be configured to cut the cannula 314 to thereby adjust the cannula's length, e.g., by allowing a proximal portion of the cannula 314 to be removed from a distal remainder of the cannula 314 coupled to the housing 312. In the illustrated embodiment, the first and second actuators each include a depressible tab 321 coupled to the housing 312 and configured to be depressed, e.g., moved radially inwards, to cut the cannula 314. The actuators can also each include a cutting mechanism 323 coupled to respective tabs 321 and contained within the interior cavity 309 of the housing 312. The cutting mechanisms 323 each include sharp blades in the illustrated embodiment, but they can have a variety of configurations, e.g., a pointed needle, an electronic cutter, etc., same or different from one another. Moreover, the cutting mechanisms 323 can be configured to cut, slice, or otherwise puncture through a sidewall of the cannula 314 as in the illustrated embodiment, or the cutting mechanisms 323 can be configured to score, crimp, or otherwise weaken the cannula's sidewall such that the cannula 314 can be broken at the scored or weakened area created by the cutting mechanisms 323. With the tabs 321 in a first, default position, the cutting mechanisms 323 can be configured to not contact the cannula 314 such that if the cannula 314 moves relative to the housing 312, e.g., if the first knob 307 is rotated, the cutting mechanisms 323 do not cut or otherwise damage the cannula 314. Similarly, if the second knob 305 rotates when the tabs 321 are in the first position, the cutting mechanisms 323 can be configured to not cut or otherwise damage the cannula 314. Pressing the tabs 321 radially inward can move the tabs 321 from the first position to a second position in which the cutting mechanisms 323 contact and cut the cannula 314.

Figure 23:
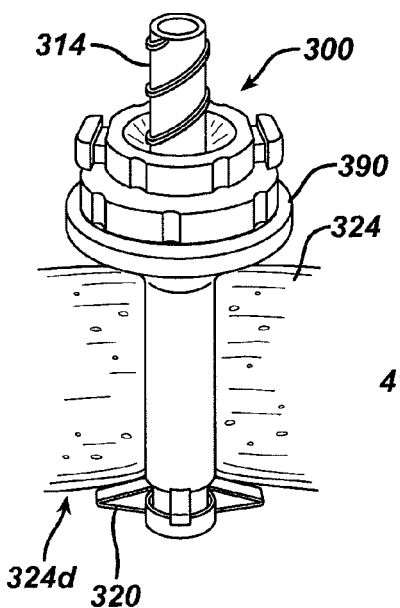
FIG. 23 is a perspective, partially cross-sectional view of the surgical access device of FIG. 22 with the tissue compressed between the housing and the anchor in a deployed configuration and with a proximal portion of the cannula extending proximally beyond the housing.
Figure 24:
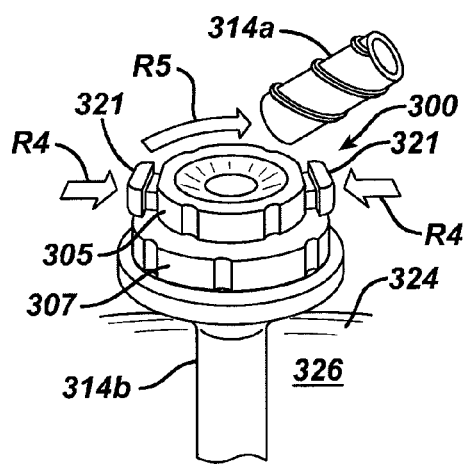
FIG. 24 is a perspective, partially cross-sectional view of the surgical access device of FIG. 23 with the housing cutting the proximal portion of the cannula from a distal remainder of the cannula positioned within the tissue opening.

In use, as shown in FIG. 22, the cannula 314 can be inserted through an opening 322 in tissue 324, similar to other cannulas discussed herein, with or without use of an obturator (not shown) or other surgical tool. An anchor 320 can be deployed within a body cavity 326 underlying the tissue 324, similar to the anchors discussed above. The first knob 307 can be rotated clockwise as shown by directional arrows R3 to threadably move the cannula 314 in a proximal direction relative to the housing 312. The cannula 314 can be moved any distance relative to the housing 312, but in an exemplary embodiment, the cannula 314 is moved until its length distal to the housing 312 reduces and its length proximal to the housing 312 increases such that the anchor 320 can abut a distal surface 324d of the tissue 324, as shown in FIG. 23. In this way, the tissue 324 can be compressed between the collar 390 and the anchor 320 to securely position the device 300 within the tissue 324. As shown in FIG. 24, the actuators can then be actuated, e.g., the tabs 321 can be pressed radially inwards as shown by directional arrows R4 to move the tabs 321 from the first position to the second position such that the cutting mechanisms 323 contact and cut the cannula 314. With the tabs 321 in the second position, the second knob 305 can be rotated clockwise as shown by directional arrow R5, thereby cutting around a perimeter or circumference of the cannula 314 to separate or break the cannula 314 into first and second portions 314a, 314b. In some embodiments, the cutting mechanisms 323 can be configured to cut around the perimeter or circumference of the cannula 314 without rotating the second knob 305, e.g., with two c-shaped, semicircular cutting mechanisms. The cutting mechanisms 323 in the illustrated embodiment are configured to cut through a sidewall of the cannula 314 such that the first and second cannula portions 314a, 314b are separate tubular members. In an embodiment where the cutting mechanisms score, crimp, or otherwise weaken the cannula 314, the cannula 314 can be manipulated by hand or instrument to separate or break the cannula at the scored, crimped, or weakened portion to yield two separate tubular members. The first cannula portion 314a can be removed from the surgical area, leaving the second cannula portion 314b positioned in the tissue 324.

With the device 300 positioned in the tissue 324 such that the tissue 324 is compressed between the anchor 320 and the collar 390 with the cannula 314 having a selected longitudinal length, as shown in FIG. 24, one or more surgical instruments (not shown) can be inserted therethrough to perform a surgical procedure in the body cavity 326. The device 300 can be disassembled and removed from the tissue 324 similar to that discussed above.

Figure 25:
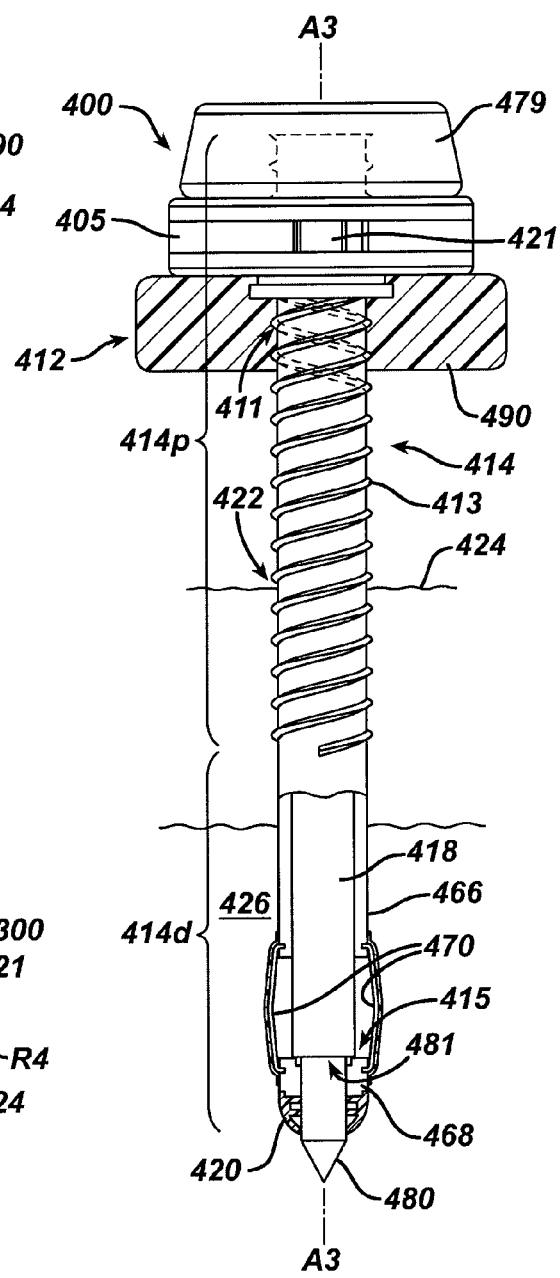
FIG. 25 is a perspective, partially transparent, partially cross-sectional view of another embodiment of a surgical access device including a housing having a cannula distally extending therefrom with an obturator disposed through the housing and the cannula and with an anchor in an undeployed configuration at a distal end of the cannula, the cannula positioned within a tissue opening with the housing located proximal to the tissue opening.

In another exemplary embodiment, shown in FIG. 25, a surgical access device 400 can include a housing 412 configured to cut a cannula 414 having a self-deploying anchor 420 disposed at a distal end thereof. The device 400, the housing 412, the cannula 414, and the anchor 420 can have a variety of configurations, and can be generally configured and used similar to the device 300 of FIG. 21 and other devices discussed herein. As shown in FIG. 25, the cannula 414 can include an elongate tubular member having a proximal, threaded portion 414p with an external thread 413, e.g., double start threads, and having a distal, unthreaded portion 414d.

The cannula's thread 413 can be configured to engage a corresponding thread 411 within a fluid-tight interior cavity of a collar 490 in a distal portion of the housing 412 such that the cannula 413 can threadably move relative to the housing 412. The collar 490 can be configured as a knob configured to rotate about a longitudinal axis A3 of the device 400 relative to a cutting assembly 405 to move the cannula 414 relative to the housing 412, similar to the first knob 307 of FIG. 21.

Figure 26:
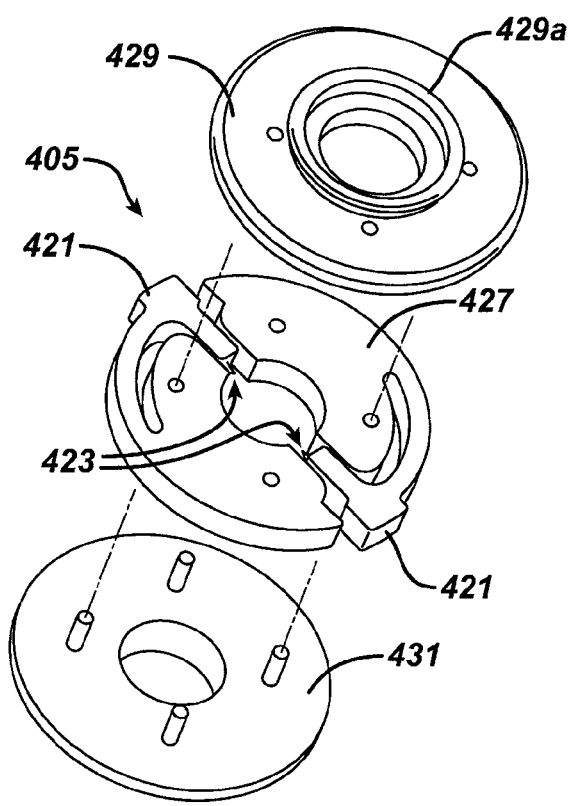
FIG. 26 is an exploded perspective view of a cutting assembly of the housing of FIG. 25.

Similar to the second knob 305 of FIG. 21, the cutting assembly 405, shown in FIGS. 25 and 26, can be configured to rotate about the device's axis A3 to rotate first and second actuators relative to the cannula 414 to cut the cannula 414. The actuators can each include a depressible tab 421 and a cutting mechanism 423 configured and used similar to the tabs 321 and the cutting mechanisms 323 of FIG. 21. The actuators can be included as part of a cutting disc 427 sandwiched between a cap 429 and a base 431 of the cutting assembly 405. The cap 429 can include a raised valve assembly ring 429a configured to removably engage a proximal housing (not shown) including one or more sealing ports each having at least one sealing element. Although, as mentioned above, the device 400 can include any number of sealing elements located anywhere within the device 400, such as an instrument seal 415 at a proximal end of the anchor 420.

Figure 27:
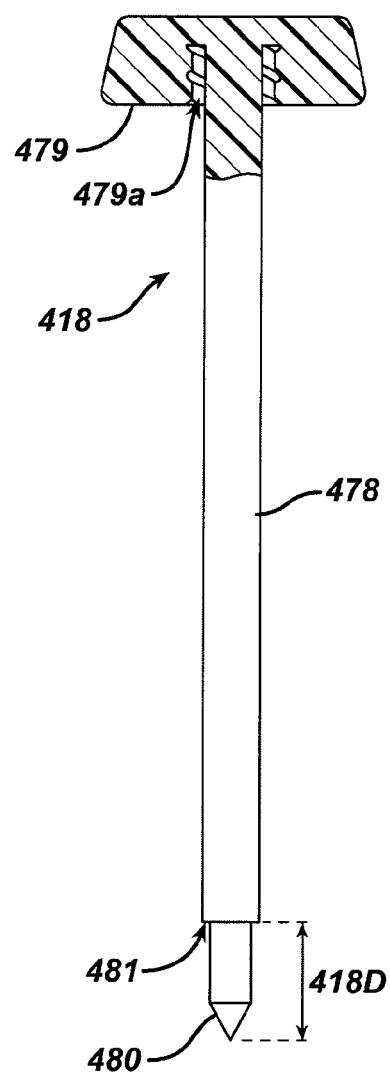
FIG. 27 is a side, partially cross-sectional view of the obturator of FIG. 25.

The device 400 can also include an obturator 418, shown in FIGS. 25 and 27. The obturator 418 can generally be used and configured similar to the obturator 18 of FIG. 1. As in the illustrated embodiment, the obturator 418 can include an elongate shaft 478 having a proximal end including a handle 479 and a distal end including a penetrating tip 480. The handle 479 can include threads 479a configured to threadably mate to the thread 413 of the cannula 414 to facilitate movement of the anchor 420 between deployed and undeployed configurations. The handle 479 can have a maximum diameter greater than a diameter of the housing's inner lumen at the inner lumen's proximal end in which the obturator 418 can be slidably disposed to prevent the obturator 418 from passing into the housing 412 through a proximal end thereof such that the obturator 418 cannot be easily manipulated. A shoulder 481 can be formed on the shaft 478 in a distal portion thereof, e.g., be located a distance 418D proximal from the distal-most end of the obturator 418, and be configured to engage a distal rim 468 of the anchor 420 to facilitate deployment of the anchor 420, as discussed further below.

The anchor 420 in the embodiment shown in FIG. 25 includes a self-deploying anchor configured to move between deployed and undeployed configurations through use of a shape memory material, e.g., Nitinol, spring steel, etc., although the anchor 420 can be configured to self deploy in any way, as will be appreciated by a person skilled in the art. The anchor 420 can include a plurality of wires 470 spaced longitudinally apart from one another and extending between proximal and distal rims 466, 468 with terminal ends of each of the wires 470 attached to the proximal and distal rims 466, 468, similar to that discussed above regarding the anchor 20 of FIG. 1. The wires 470 can be formed of a shape memory material and be configured in a default, deployed configuration such that that anchor 420 is biased to the deployed configuration.

In use, as shown in FIG. 25, the cannula 414 can be inserted through an opening 422 in tissue 424 with the obturator 418 disposed therein. The obturator 418 can be inserted tip 480 first through a proximal end of the cannula 414 and distally advanced therethrough until the obturator's shoulder 481 abuts the anchor's distal rim 468. Continued distal advancement of the obturator 418 can thus distally push the distal rim 468 away from the proximal rim 466, thereby moving the anchor 420 from the deployed configuration to the undeployed configuration, as shown in FIG. 25. In an exemplary embodiment, the anchor 420 can be locked in the undeployed configuration by threading the cannula's and obturator handle's threads 413, 479a, which can help facilitate insertion of the device 400 through the tissue opening 422 with the anchor 420 having a reduced diameter from the deployed configuration.

Figure 28:
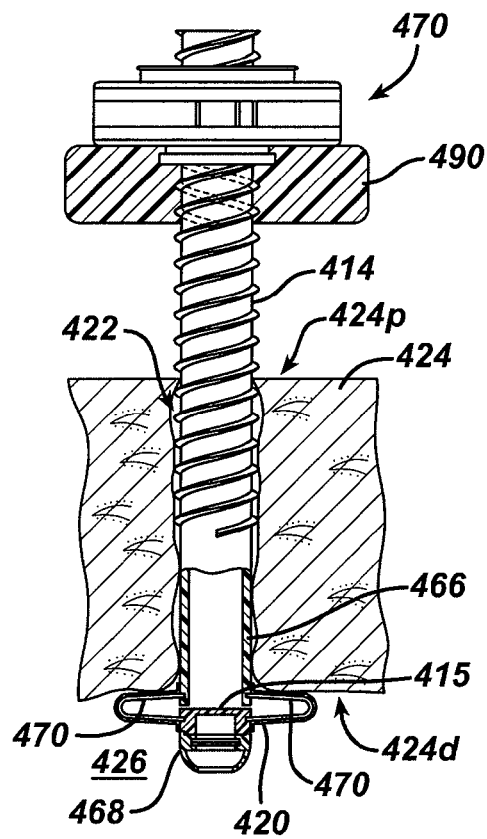
FIG. 28 is a side, partially transparent, partially cross-sectional view of the surgical access device of FIG. 25 with the obturator removed therefrom and with the anchor in a deployed configuration.

With the obturator 418 expanding the anchor 420, the device 400 can be inserted through the tissue 424, leading with the obturator's tip 480, such that at least the anchor 420 is positioned in a body cavity 426 underlying the tissue 424, as illustrated in FIG. 25. With the anchor 420 positioned in the body cavity 426, the anchor 420 can be moved from the first configuration to the second configuration, e.g., the anchor 420 can be deployed. Removing the obturator 418 from the anchor 420 can allow the wires 470 to spring or move to their default configuration, with the distal rim 468 moving toward the proximal rim 466 to move the anchor 420 to the deployed configuration, as shown in FIG. 28. The device 400 can be moved in a proximal direction until the anchor 420 abuts a distal surface 424d of the tissue 424 facing the body cavity 426, as also shown in FIG. 28. The obturator 418 can be fully removed from the cannula 414, unscrewing the handle 479 from the cannula 414 if necessary, before or after the deployed anchor 420 abuts the tissue's distal surface 424d.

Figure 29:
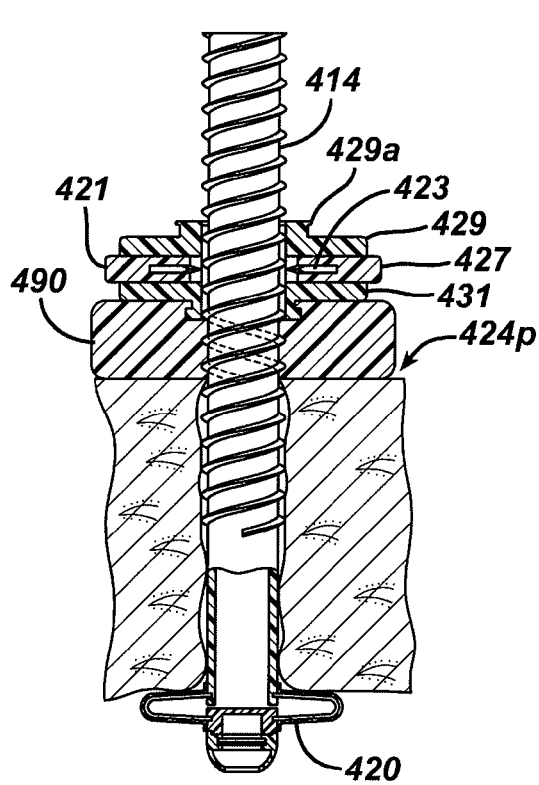
FIG. 29 is a side, partially transparent, partially cross-sectional view of the surgical access device of FIG. 28 with the housing distally advanced along the cannula and abutting a proximal surface of the tissue.
Figure 30:
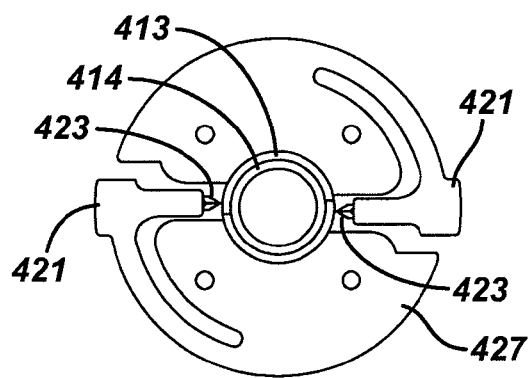
FIG. 30 is a top view of a cutting disc of the cutting assembly of FIG. 26 with the cannula disposed through a central opening thereof and with cutting mechanisms out of cutting contact with the cannula.
Figure 31:
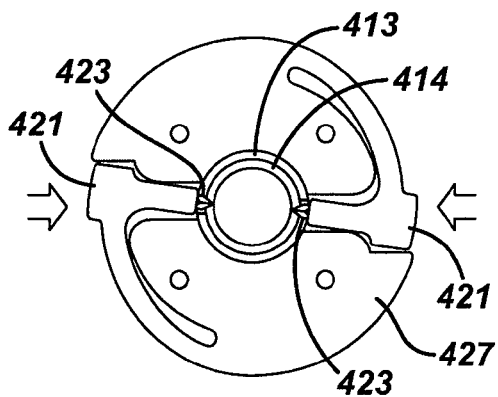
FIG. 31 is a top view of the cutting disc of FIG. 30 with the cutting mechanisms in cutting contact with the cannula.

The housing 412 and the cannula 414 can be threadably moved, e.g., through threading the cannula 414 and the collar 490, until the collar 490 abuts a proximal surface 424p of the tissue 424 such that the tissue 424 is compressed between the housing 412 and the anchor 420, as shown in FIG. 29. When the housing 412 is moved to abut the tissue 424, the tabs 427 can be in a first position, shown in FIG. 30, such that the cutting mechanisms 423 do not cut or otherwise damage the cannula 414. When the housing 412 and the cannula 414 are in a desired position relative to one another and to the tissue 424, the tabs 421 can be depressed to move the cutting mechanisms 423 to a second position, shown in FIG. 31, in which they penetrate the cannula 414. The cutting assembly 405 can then be rotated relative to the cannula 414 to cut the cannula 414 such that a proximal cut portion 414a thereof can be removed from a distal remainder 414b thereof, as illustrated in FIG. 32.

Figure 32:
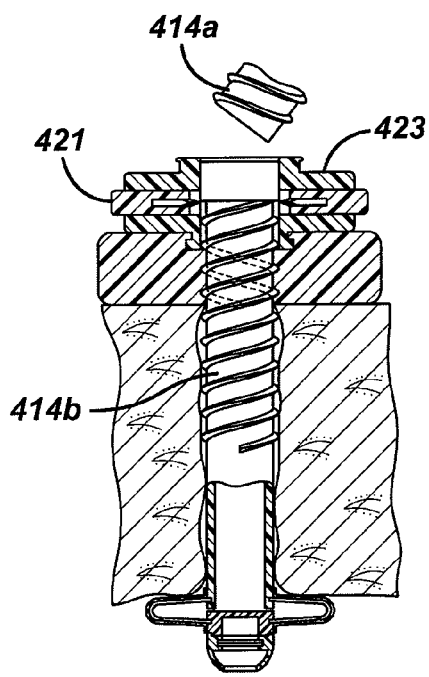
FIG. 32 is a side, partially transparent, partially cross-sectional view of the surgical access device of FIG. 29 with a proximal portion of the cannula being removed from a distal remainder of the cannula positioned within the tissue opening.

With the device 400 positioned in the tissue 424 such that the tissue 424 is compressed between the anchor 420 and the collar 490 with the cannula 414 having a selected longitudinal length, as shown in FIG. 32, one or more surgical instruments (not shown) can be inserted therethrough to perform a surgical procedure in the body cavity 426. The device 400 can be disassembled and removed from the tissue 424 similar to that discussed above.

A rotation knob configured to aid in cutting the cannula 414 can be optionally coupled to the housing 412. As illustrated in one embodiment in FIG. 33 in which like-named elements can be configured and used similar to those in the device of FIG. 25, a rotation knob 433 configured to aid in cutting a cannula 414' can be optionally coupled to a housing 412', such as by being snapped onto a valve assembly ring 429a' of a cutting assembly 405'. Although the rotation knob 433 is removably attached to a cap 429' including the valve assembly ring 429a' in the illustrated embodiment, the rotation knob 433 can be fixedly mated to the cap 429'. Generally, the rotation knob 433 can be configured to facilitate cutting mechanisms 423' of a cutting disc 427' of the cutting assembly 405' cutting around an entire perimeter or circumference of the cannula 414'.

The rotation knob 433 can have a variety of sizes, shapes, and configurations. The rotation knob 433 can include at least one radially-inward extending peg, protrusion, or pin 433a, generally referred to as a "peg," spaced equidistantly or any other distance around an inner perimeter or circumference of the rotation knob 433. The rotation knob 433 can include any number of pegs 433a. In an exemplary embodiment, the rotation knob 433 includes a number of pegs 433a equal to a number of cutting mechanisms 423' such that each of the pegs 433a can be operable to move one of the cutting mechanisms 423' into contact with the cannula 414'. The pegs 433a can be configured to slidably engage an outer perimeter or circumference of the cutting disc 427'. The outer perimeter or circumference of the cutting disc 427' can include at least one radially-outward extending detent 435, e.g., a number of detents 435 equal to a number of pegs 433a, configured to act as a surpassable barrier to at least one of the pegs 433a. Located a distance around its perimeter or circumference, the cutting disc 427' can also include at least one radially-outward extending stop 437, e.g., a number of stops 437 equal to a number of detents 435 and pegs 433a, configured to act as an unsurpassable barrier to at least one of the pegs 433a. The cutting disc's perimeter or circumference can include a flared portion along a partial length thereof in the form of a ramp 439 between associated ones of the detents 435 and stops 437 such that the cutting disc's perimeter or circumference flares radially outward along the ramps 439.

Figure 33:
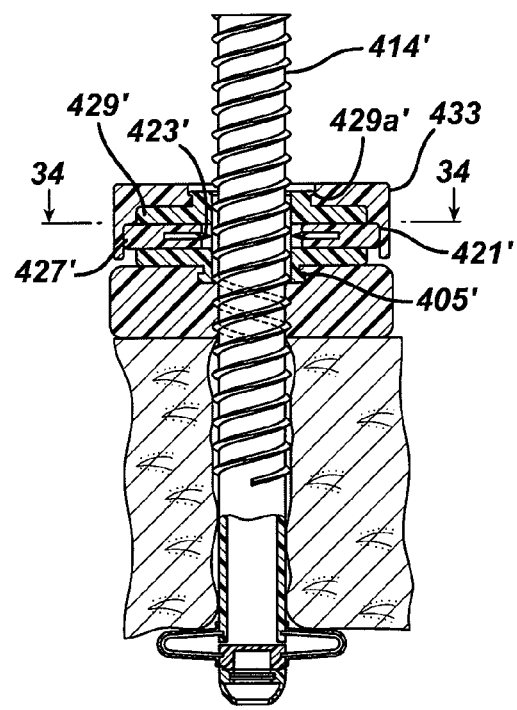
FIG. 33 is a side, partially transparent, partially cross-sectional view of another embodiment of a surgical access device including a housing having a cannula distally extending therefrom with an anchor in a deployed configuration at a distal end of the cannula, the cannula positioned within a tissue opening with the tissue being compressed between the housing and the anchor.
Figure 34:
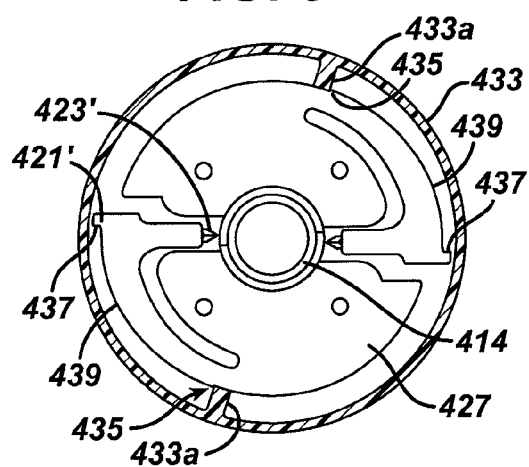
FIG. 34 is a top view of a cutting disc of the housing of FIG. 33 with the cannula disposed through a central opening thereof and with cutting mechanisms out of cutting contact with the cannula.
Figure 35:
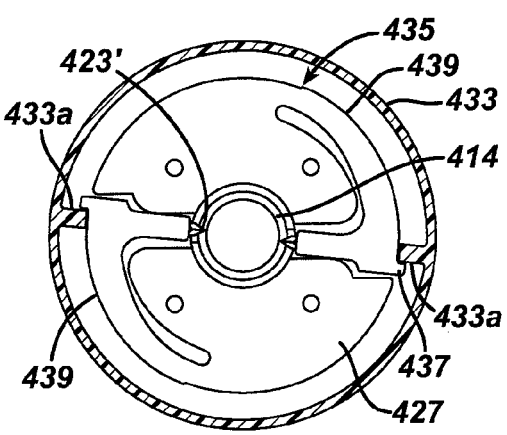
FIG. 35 is a top view of a cutting disc of the housing of FIG. 33 with the cannula disposed through a central opening thereof and with cutting mechanisms in cutting contact with the cannula.

In use, with the cutting mechanisms 423' and tabs 421' of the cutting disc 427' in a first position, shown in FIGS. 33 and 34, the rotation knob 433 can be in a first position such that the cutting mechanisms 423' can be configured to not cut or otherwise damage the cannula 414'. In the first position, the pegs 433a can engage the cutting disc's perimeter or circumference anywhere therearound on a non-flared portion thereof, e.g., not on the ramps 437. Rotating the rotation knob 433 in a first direction, e.g., clockwise, can move the rotation knob 433 to a second position to allow the pegs 433a to surpass the detents 435 and engage the ramps 439. Sliding in the first direction along the ramps 439, the pegs 433a can urge the tabs 421' radially inward such that the cutting mechanisms 423' can penetrate the cannula 414'. The stops 437 can be configured to stop rotation of the rotation knob 433 in the first direction when the pegs 433a abut the stops 437, as shown in FIG. 35. Continued rotation of the rotation knob 433 in the first direction can thus also rotate the cutting disc 427' in the first direction such that the cutting mechanisms 423' can rotate relative to the cannula 414' and cut the cannula 414'. Rotation of the rotation knob 433 in a second, opposite direction, e.g., counterclockwise, can allow the pegs 433a to slide along the ramps 439 and then out of engagement therewith such that the cutting mechanisms 423' can move from the second position to the first position and such that a cut proximal portion of the cannula 414' can be removed from a distal remainder portion as discussed above.

The devices of FIGS. 21-35 include housings configured to cut a cannula and that, in exemplary embodiments, remain coupled to the cannula after the cannula has been cut and a portion of the cannula has been removed. In another exemplary embodiment, a surgical access device can include a housing removably coupled to a cannula and configured to be removed from the cannula after cutting the cannula to adjust the cannula's longitudinal length. The device can be configured such that the cannula can be positioned within a tissue opening when the housing cuts the cannula.

Figure 36:
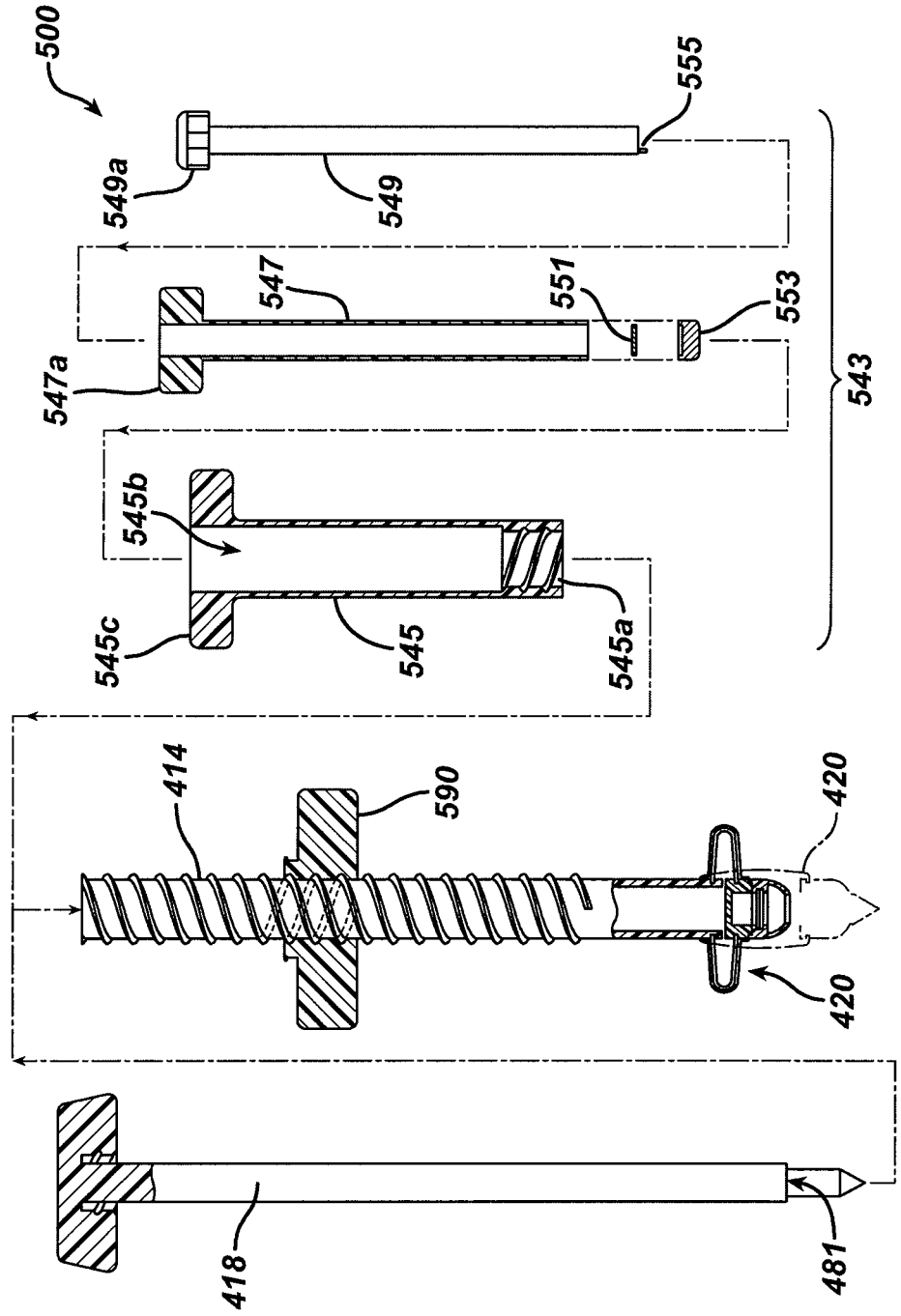
FIG. 36 is a side, partially transparent, partially cross-sectional view of another embodiment of a surgical access device including a cannula having an anchor at a distal end thereof and having a collar disposed therearound, an obturator configured to be disposed in the cannula, and a cutting assembly configured to be disposed in and around the cannula.

In an exemplary embodiment illustrated in FIG. 36, a surgical access device 500 can include the cannula 414 of FIG. 26 with a collar 590 threadably mated thereto, the obturator 418 of FIG. 27 configured to be slidably disposed in the cannula 414, and a cutting assembly 543 configured to removably mate to the cannula 414 and cut the cannula 414 into separable portions. The cannula 414 is illustrated in FIG. 36 with the anchor 420 in solid lines in the deployed configuration and with the anchor 420 in phantom lines in the undeployed configuration. The cutting assembly 543 can have a variety of sizes, shapes, and configurations, and the device 500 can be generally configured and used similar to other like-named elements discussed herein.

Generally, the cutting assembly 543 can be configured to removably mate to the cannula 414 to cut the cannula 414 so as to reduce the cannula's longitudinal length. As shown in FIG. 36, the cutting assembly 543 can include an outer cannula 545 configured to threadably mate with internal threads 545a to the threads 413 of the cannula 414, an inner cannula 547 configured to be slidably disposed in the outer cannula 545 and the cannula 414, and an actuator shaft 549 configured to be slidably disposed in the inner cannula 547. The inner cannula 547 can be configured to be slidably disposed in an inner lumen 545b of the outer cannula 545. In an exemplary embodiment, the inner cannula 547 can include a proximal handle 547a configured to prevent the inner cannula 547 from passing proximally into the outer cannula's inner lumen 545b. Similarly, the outer cannula 545 can include a proximal handle 545c configured to prevent passage of the outer cannula 545 into a proximal end of the cannula 414, and the actuator shaft 549 can include a proximal handle 549a configured to prevent passage of the actuator shaft 549 into a proximal end of the inner cannula 547.

Figure 37:
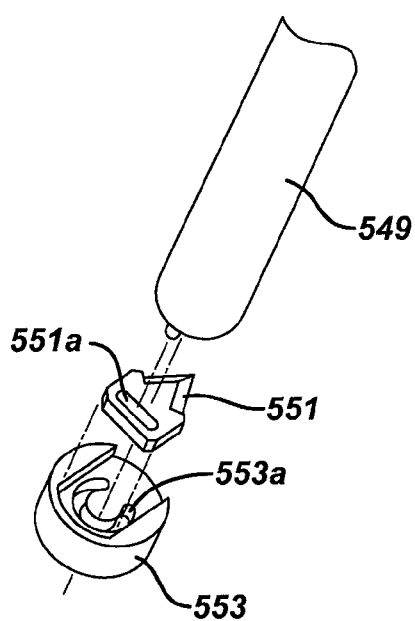
FIG. 37 is a perspective, exploded, partial view of a distal end of an inner cannula of the cutting assembly of FIG. 36 and an actuator shaft of the cutting assembly of FIG. 36 configured to engage the distal end of the inner cannula.

The inner cannula 547, as shown in FIGS. 36 and 37, can include a cutting mechanism 551 at a distal end thereof, e.g., a blade coupled to a distal base 553 of the inner cannula 547. The cutting mechanism 551 can be configured to cut the cannula 414, similar to the cutting mechanisms 323, 423 discussed above and as discussed further below such that the cutting mechanism 551 can be selectively engaged with the cannula 414 to cut the cannula 414. The actuator shaft 549 can include an actuating pin 555 at a distal end thereof. The actuating pin 555 in the illustrated embodiment includes a distally, longitudinally extending cylindrical rod or needle from the actuator shaft's distal end, but the actuating pin 555 can have any size, shape, and configuration. The actuating pin 555 can be configured to selectively engage the cutting mechanism 551 with the cannula 414. As discussed further below, the actuating pin 555 can be configured to pass through a slot 551a formed in the cutting mechanism 551 and into a groove 553a formed in the inner cannula base 553 to engage the cutting mechanism 551 and move the cutting mechanism 551 relative to the cannula 414.

Figure 38:
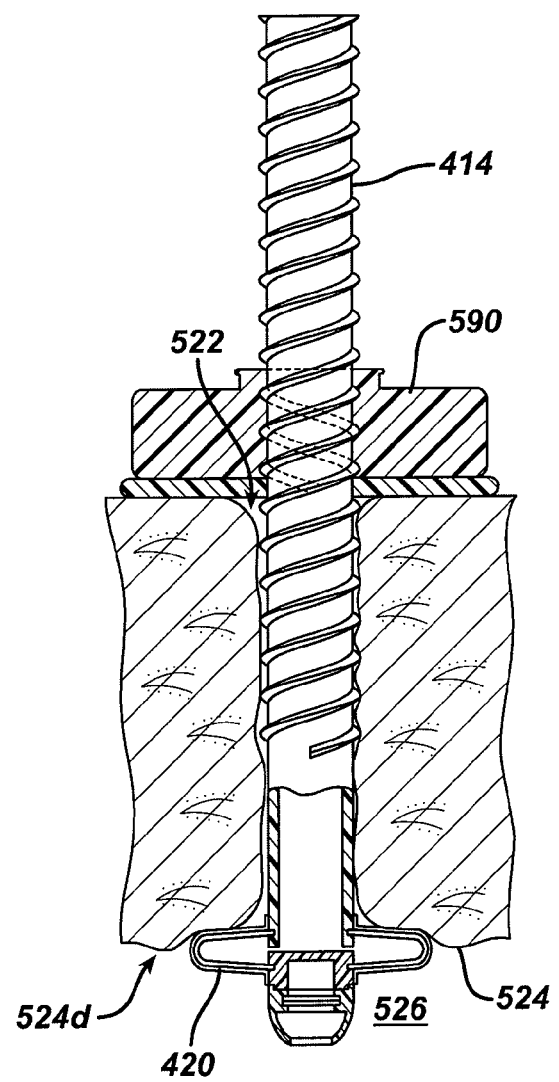
FIG. 38 is a side, partially transparent, partially cross-sectional view of the cannula and collar of FIG. 36 with the cannula positioned within a tissue opening with the collar abutting a proximal surface of the tissue and the anchor in a deployed configuration abutting a distal surface of the tissue.

In use, the cannula 414 can be positioned in a tissue opening and the anchor 420 can be self-deployed similar to that discussed above regarding the cannula's positioning within the tissue opening 422 of FIG. 25. FIG. 38 illustrates the cannula 414 positioned within a tissue opening 522 in tissue 524 with the obturator 418 removed therefrom, with the anchor 420 deployed in a body cavity 526 underlying the tissue 524 and abutting a distal surface 524d of the tissue 524, and with the tissue 524 compressed between the collar 590 and the anchor 420.

With the cannula 414 desirably positioned in the tissue opening 522, the cutting assembly 543 can be releasably mated to the cannula 414, as shown in FIG. 39, with the cannula 414 threadably engaging the threads 545a of the outer cannula 545. A proximal stop, e.g., a valve assembly ring 590a, formed on the collar 590 can be configured to prevent movement of the outer cannula 545 in a distal direction when a distal surface of the outer cannula 545 abuts the valve assembly ring 590a. The inner cannula 547 and the actuator shaft 549 can be inserted into the outer cannula 545, separately or together, before or after the outer cannula 547 releasably mates to the cannula 414.

Figure 41:
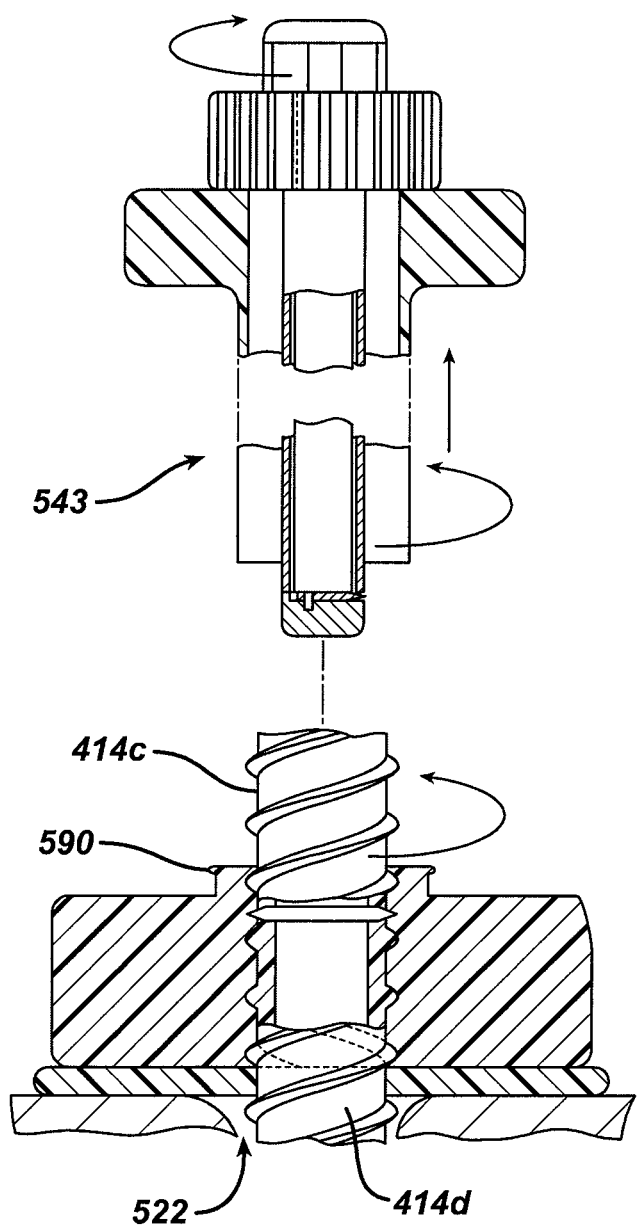
FIG. 41 is a side, partially transparent, partially cross-sectional view of the cutting assembly of FIG. 40 being removed from the cannula and with a proximal portion of the cannula cut from a distal remainder of the cannula positioned within the tissue opening.

The threaded engagement of the outer cannula 545 and the cannula 414 can prevent the cannula 414 from rotating relative thereto once the outer cannula 545 and the cannula 414 are threadably mated. As shown in FIG. 40, the actuator shaft 549 can be rotated counterclockwise and/or clockwise to move the cutting mechanism 551 relative to the cannula 414 to penetrate the cannula 414 and to cut around a perimeter or circumference of the cannula 414. The inner cannula 547, e.g., by its handle 547a, can be held by hand and/or instrument to allow the actuator shaft 549 to rotate relative thereto. With the cannula 414 cut into separate proximal and distal portions 414c, 414d, as shown in FIG. 41, the cutting assembly 543 can be disengaged from the cannula 414, e.g., by unthreading the outer cannula 545 and by proximally moving the components of the cutting assembly 543 separately or together. The separate proximal portion 414c of the cannula 414 can be rotated relative to the collar 590 to unthread the proximal portion 414c therefrom, thereby allowing the proximal portion 414c to be removed while leaving the distal portion 414d positioned within the tissue opening 522.

With the tissue 524 compressed between the anchor 420 and the collar 590 with the cannula 414 having a selected longitudinal length, as shown in FIG. 41, one or more surgical instruments (not shown) can be inserted therethrough to perform a surgical procedure in the body cavity 526. The device 500 can be disassembled and removed from the tissue 424 similar to that discussed above.

As discussed above, a surgical access device can be configured such that a length of the device's cannula can be cut into two or more pieces, with loose lengths of the cannula being removable from the device and from the surgical site. In another exemplary embodiment, shown in FIGS. 42 and 43, a housing 612 of a surgical access device 600 can be configured to cut a cannula 614 distally extending from the housing 612 and to contain a cut proximal portion of the cannula 614 within the housing 612. In this way, loose cannula pieces can be less likely to be misplaced or interfere with a surgical procedure. Generally, the housing 612 and the cannula 614 can have a variety of sizes, shapes, and configurations, and the device 600 can be configured and used similar to other like-named elements discussed herein.

Although the cannula 614 can have a variety of sizes, shapes, and configurations, in the illustrated embodiment, the cannula 614 includes a plurality of beads, modules, or segments 614a generally referred to as "segments," movably coupled together such that the cannula 614 can bend and can adjust in longitudinal length. The segments 614a can be fixedly coupled together or, as in the illustrated embodiment, the segments 614a can be configured to be modular such that they can be selectively connected and disconnected from one another to adjust a longitudinal length of the cannula 614. Generally, the segments 614a can allow the cannula 614 to be configured as an axially-expandable, articulating tubular member configured to be securely positioned within an opening 622 in tissue 624 of any thickness, e.g., in a range of about 1 to 7 cm thick, and articulate therein to improve access to a body cavity (not shown) underlying the tissue 624. The cannula 614 can optionally include an anchor (not shown) at a distal end thereof. The anchor can be configured to movably couple to a distal-most one of the segments 614a. Exemplary embodiments of cannulas including a plurality of segments are described in more detail in previously mentioned U.S. patent application Ser. No. 12/636,174 entitled "Methods And Devices For Providing Access Through Tissue To A Surgical Site," filed dec. 11, 2009 [Attorney Docket No. 100873-380 (END6634USNP)], U.S. patent application Ser. No. 12/636,184 entitled "Methods And Devices For Providing Access Through Tissue To A Surgical Site," filed Dec. 11, 2009 [Attorney Docket No. 100873-381 (END6634USNP1)], and U.S. patent application Ser. No. 12/636,191 entitled "Methods And Devices For Providing Access Through Tissue To A Surgical Site," filed Dec. 11, 2009 [Attorney Docket No. 100873-382 (END6634USNP2)].

A proximal-most one of the segments 614b can include an elongate neck 614c extending proximally therefrom. The neck 614c can have a variety of sizes, shapes, and configurations. Although the neck 614c has threads 685, the neck 614c can be unthreaded. Generally, the neck 614c can be configured to be cut by the housing 612 to reduce a longitudinal length of the cannula 614.

The housing 612 can also have a variety of sizes, shapes, and configurations. As shown in the illustrated embodiment, the housing 612 can include a rotatable knob 683 and a collar 690 including a sealing element 690a and an anti-rotation ring 690b. Generally, the sealing element 690a can be configured to provide a seal between the housing 612 and the tissue opening 622, and the anti-rotation ring 690b can be configured to allow the rotatable knob 683 to be rotated relative to the cannula 614 to cut a proximal portion of the cannula 614 to reduce the cannula's longitudinal length.

Although the device 600 can include any number of seals located anywhere in the device 600, in an exemplary embodiment, the sealing element 690a can be configured as a compressible seal element including a gel and/or a foam. Generally, the sealing element 690a can include a flexible, composite material, e.g., a gel, a foam, an elastomer, isoplast (polyurethane), polyisoprene (natural rubber), santoprene (thermoplastic rubber), etc., configured to prevent fluid passage therethrough, to flex upon application of an external force without breaking, tearing, or otherwise allowing fluid to pass therethrough, and to dynamically flex to return to a default or resting position when the external force is removed. While a person skilled in the art will appreciate that any gel material can be used, a non-limiting example of a gel material includes a combination of an internal low molecular weight chemical species such as mineral oil or other oil, plasticizer, etc. and Kraton™ Rubber, e.g., styrene-ethylene/butylene-styrene (S-E/B-S) tri-block polymer, available from Kraton Polymers LLC of Houston, Tex. Generally, a foam material can have a lower elastic modulus than a gel material, e.g., about 10% of the elastic modulus of a gel material. While a person skilled in the art will also appreciate that any foam material can be used, non-limiting examples of a foam material includes Kraton™ Rubber, silicone elastomers, polyurethanes, polyolefins such as polypropylene and polyethylene, polyolefin elastomers such as Santoprene™, e.g., a crosslinked co-polymer of polypropylene and EPDM (ethylene propylene diene M-class) rubber, available from Advanced Elastomer Systems, LP of Akron, Ohio, polyethylene-co-vinyl acetate copolymers, polytetrafluoroethylene (PTFE) in the form of expanded PTFE, etc.

The rotatable knob 683 can have a variety of sizes, shapes, and configurations. As in the illustrated embodiment, the rotatable knob 683 can include a head 687 defining a fluid-tight cavity 687a therein, a valve assembly ring 692 formed on a proximal end of the head 687, and an elongate neck 687b extending distally therefrom. The head 687 can also include at least one cutting mechanism 623, e.g., two blades, located in or at least extending into the cavity 687a. The knob's neck 687b can be configured to be received within the cannula's neck 614c and be threadably engaged therewith, with the threads cannula's internal threads 685 being configured to engage the head's external threads 687c. The rotatable knob 683 can be configured to be threaded into the cannula 614, e.g., by rotating the knob 683 relative to the cannula 614 about a longitudinal axis A4 of the device 600, to allow the cannula's neck 614c to proximally advance into the knob's cavity 687. In this way, the cutting mechanism 623 can come into contact with the cannula 614 to cut the cannula 614 as discussed further below.

Figure 42:
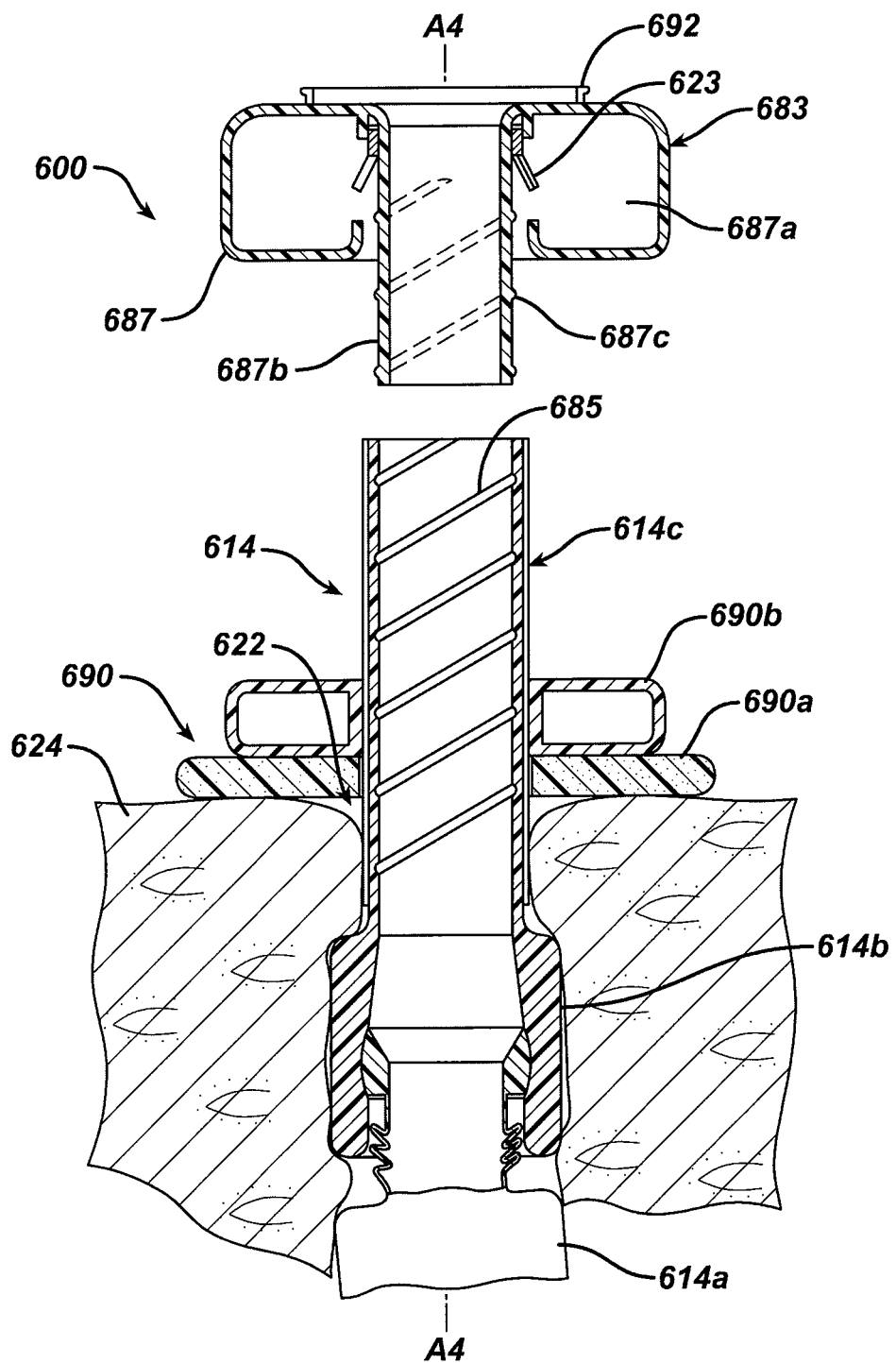
FIG. 42 is a side, cross-sectional view of another embodiment of a surgical access device including a cannula including a plurality of movably coupled segments and having a collar disposed therearound, and a cutting assembly configured to couple to and cut the cannula.
Figure 43:
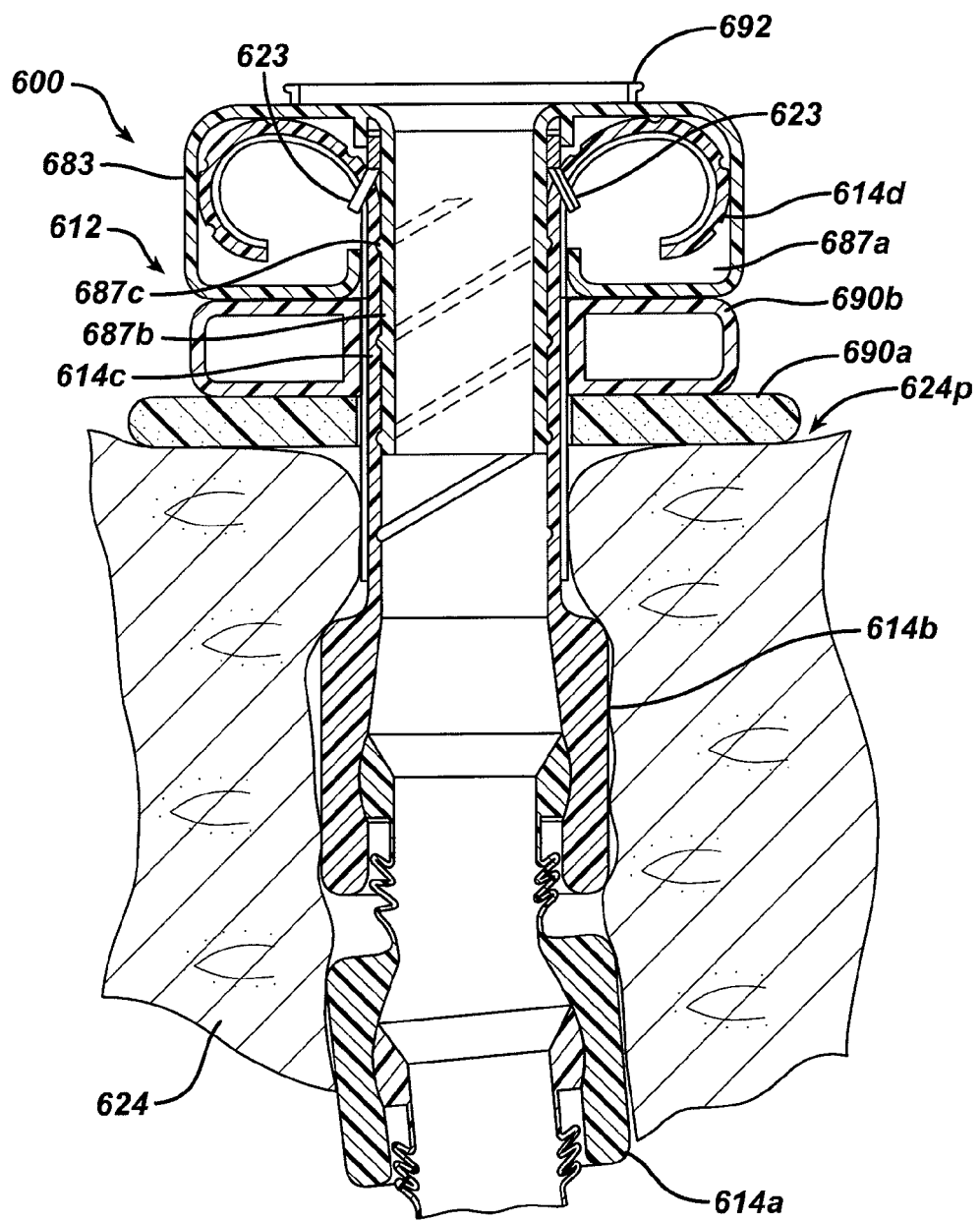
FIG. 43 is a side, cross-sectional view of the surgical access device of FIG. 42 with the cutting assembly mated to and cutting the cannula.

In use, as shown in FIG. 42, the cannula 614 can be positioned in the tissue opening 622 similar to that discussed above regarding other embodiments of surgical access devices. If present, an anchor at the distal end of the cannula can be deployed within a body cavity underlying the tissue 624. With the cannula 614 desirably positioned in the tissue opening 622, e.g., with the collar 690 abutting a proximal surface 624p of the tissue 624, the rotatable knob 683 can be releasably mated to the cannula 614, with the cannula 614 threadably engaging the threads 687c of the knob's neck 687b. As the proximal end of the cannula 614, e.g., the cannula's neck 614c, enters the cavity 687a within the device's housing 612, the cutting mechanism 623 can be configured to cut the cannula 614, as shown in FIG. 43. Similar to a pencil sharpener, the cannula 614 can be cut into a continuous strip 614d that curls into the cavity 687a to be contained therein, as shown in the illustrated embodiment, or the cut portion of the cannula 614 can include a plurality of strips or chips that are deposited in the cavity 687a. In this way, a longitudinal length of the cannula 614 can be selectively reduced. In an exemplary embodiment, the cannula 614 includes an anchor at its distal end, and the rotatable knob 683 is rotated to cut the cannula 614 until the anchor in a deployed configuration abuts the tissue's distal surface (not shown) such that the tissue 624 is compressed between the housing 612 and the anchor. Rotating the rotatable knob 683 can also move it in a distal direction so as to compress the sealing element 690a, which can help maintain a seal when the cannula 614 adjusts in length.

With the cannula 614 having a selected longitudinal length, one or more surgical instruments (not shown) can be inserted therethrough to perform a surgical procedure in the body cavity underlying the tissue 624. As mentioned above, a housing include at least one sealing port can be optionally attached to the valve assembly ring 692 before and/or after any one or more instruments are inserted through the device 600. The device 600 can be disassembled and removed from the tissue 624 similar to that discussed above.

Figure 44:
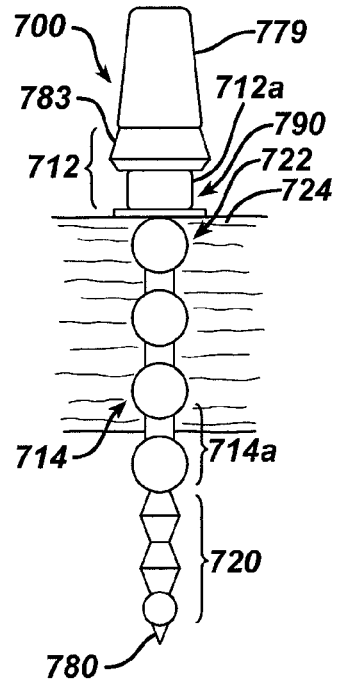
FIG. 44 is a side, partially cross-sectional view of another embodiment of a surgical access device including a cannula positioned within a tissue opening, having an anchor at a distal end thereof in an undeployed configuration, having a collar disposed therearound, and having an obturator disposed therethrough.
Figure 45:
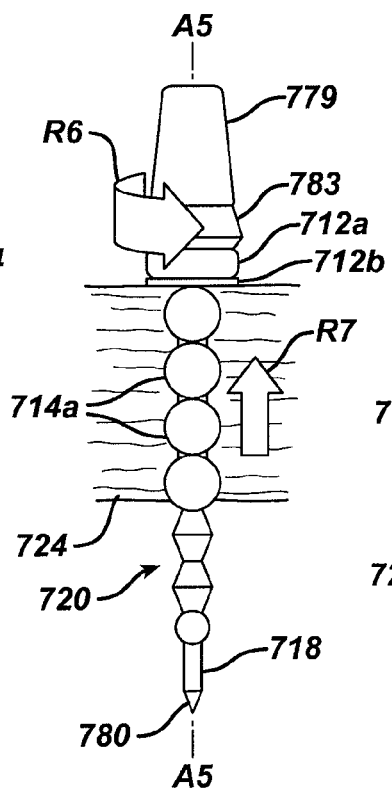
FIG. 45 is a side, partially cross-sectional view of the surgical access device of FIG. 44 with the collar being rotated to adjust a longitudinal length of the cannula.
Figure 46:
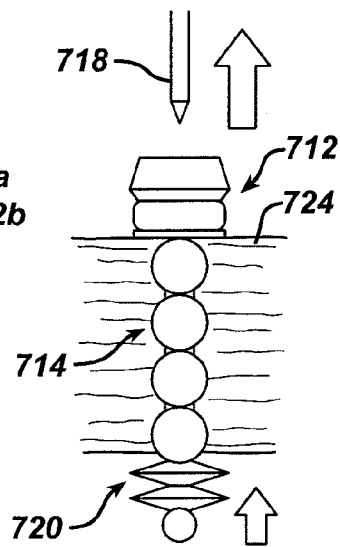
FIG. 46 is a side, partially cross-sectional view of the surgical access device of FIG. 45 with the obturator being removed from the cannula and with the anchor in a deployed configuration.

In another exemplary embodiment, shown in FIGS. 44-46, a surgical access device 700 can include a housing 712 configured to rotate relative to a cannula 714 extending distally therefrom and to cut the cannula 714 and retain a cut portion of the cannula 714 within a cavity (not shown) defined by the housing 712. An obturator 718 having a proximal handle 779 and a distal tip 780 can be configured to be slidably disposable in the housing 712 and the cannula 714 to facilitate positioning of the cannula 714 within a tissue opening 722 in tissue 724. Generally, the housing 712, the cannula 714, and the obturator 718 can have a variety of sizes, shapes, and configurations, and the device 700 can be configured and used similar to other like-named elements discussed herein. The cannula 714 can include a plurality of movably coupled segments 714a and have a self-deploying, accordion-type anchor 720 at a distal end thereof. The housing 712 can include a distal collar 790 and a proximal rotatable knob 783 having a cutting mechanism (not shown) disposed in the housing's cavity and configured to selectively cut the cannula 714.

Although the device 700 can include any number of seals located anywhere in the device 700, in an exemplary embodiment, the collar 790 can be configured as a seal element, e.g., as a compressible seal element including a gel and/or a foam. Generally, the collar 790 can include a flexible, composite material 712a, e.g., a gel, a foam, and an elastomer, configured to prevent fluid passage therethrough, to flex upon application of an external force without breaking, tearing, or otherwise allowing fluid to pass therethrough, and to dynamically flex to return to a default or resting position when the external force is removed. The flexible seal material 712a can be disposed on a distal seal ring 712b, which can provide stability to the flexible seal material 712a.

In use, as shown in FIG. 44, the cannula 714 with the anchor 720 in an undeployed configuration can be positioned in the tissue opening 722 using the obturator 718 similar to that discussed above regarding other embodiments of surgical access devices. The obturator 718, e.g., the obturator's handle 779, can be rotated in a first direction, e.g., counterclockwise as shown by directional arrow R6, relative to the cannula 714 about a longitudinal axis A5 of the device 700, as shown in FIG. 45. Rotation of the obturator 718 can be configured to also rotate the rotating knob 783, although the rotating knob 783 can be configured to rotate without being coupled to the obturator 718. The cannula 714 can thus be threadably moved in a proximal direction, shown by directional arrow R7, relative to the housing 712 such that a proximal end of the cannula 714 is cut by the cutting mechanism and deposited within the housing's cavity, thereby reducing the cannula's longitudinal length.

In an exemplary embodiment in which the cannula 714 is not threaded, e.g., lacks the threads 685 on the neck 614c of FIGS. 42 and 43, rotating the rotatable knob 783 can allow the housing to come into contact with the cannula such that the housing can form threads on the cannula when the cannula rotates relative to the housing. Having an unthreaded cannula can facilitate positioning of the cannula within tissue, and forming threads on the cannula can facilitate proximal movement of the cannula and trimming thereof by the cutting mechanism. Although the housing can form threads on the cannula in any way, in an exemplary embodiment, the threads 687c on the housing's neck 687b of FIGS. 42 and 43 can be configured as a cutting mechanism to form threads on the cannula, e.g., on the cannula's previously unthreaded neck, when the rotatable knob 783 rotates relative to the cannula about the axis A4. In this way, the cannula can be moved proximally and have its proximal end trimmed by the cutting mechanism.

Rotation of the knob 783 can also cause the segments 714a to move relative to one another to reduce the cannula's longitudinal length. Rotating the rotation knob 783 can also move it in a distal direction so as to compress the collar 790, e.g., compress the material 712a, which can help maintain a seal when the cannula 714 adjusts in length. Either before or after the cannula 714 is adjusted to a selected longitudinal length, the obturator 718 can be removed from the housing 712 and the cannula 714, as shown in FIG. 46, thereby allowing the anchor 720 to move from the undeployed configuration to the deployed configuration.

With the cannula 714 having a selected longitudinal length, one or more surgical instruments (not shown) can be inserted therethrough to perform a surgical procedure in the body cavity underlying the tissue 724. The device 700 can be disassembled and removed from the tissue 724 similar to that discussed above.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a housing, a segment, a collar, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An adjustable access device, comprising:
   a cannula comprising a plurality of segments removably coupled to one another such that a mating connection between each of the plurality of segments forms a fluid tight seal and such that a length of the cannula is adjustable, the cannula defining a working channel extending therethrough for receiving an instrument; and
   a collar slidably disposed on the cannula such that the collar can slide along an external surface of each of the plurality of segments when the segments are removably coupled to one another, the collar being configured to selectively engage one of the plurality of segments to allow adjustment of a distance between the collar and a distal end of the cannula.

2. The adjustable access device of claim 1, wherein each segment includes an engagement feature to removably mate to an adjacent segment.

3. The adjustable access device of claim 2, wherein the engagement feature comprises at least one radially extending protrusion configured to engage an opening in an adjacent segment.

4. The adjustable access device of claim 1, wherein the collar has an alignment feature configured to align with a complementary alignment feature of the cannula such that the collar is only slidably disposable on the cannula in at least one predetermined orientation.

5. The adjustable access device of claim 1, wherein each of the segments proximal to the one of the plurality of segments engaged by the collar are removable from the one of the plurality of segments engaged by the collar and each of the plurality of segments distal to the collar.

6. The adjustable access device of claim 5, wherein the segments located proximal to the one of the plurality of segments engaged by the collar are rotatable about a longitudinal axis of the cannula to release the segments located proximal to the one of the plurality of segments engaged by the collar from the one of the plurality of segments engaged by the collar and each of the plurality of segments distal to the collar.

7. The adjustable access device of claim 5, wherein an alignment feature of the collar engages a complementary alignment feature of the one of the plurality of the segments to allow the segments proximal to the one of the plurality of segments engaged by the collar to be removed from the one of the plurality of segments engaged by the collar.

8. The adjustable access device of claim 1, further comprising a housing configured to mate to the collar, the housing having at least one seal disposed therein that is configured to form at least one of a seal around an instrument disposed through the housing and a seal across the housing when no instrument is disposed therethrough.

9. The adjustable access device of claim 1, further comprising an expandable anchor coupled to the distal end of the cannula.

10. The adjustable access device of claim 1, wherein the external surface of each of the plurality of segments is an outer circumferential surface.

11. An adjustable access device, comprising:
    an elongate tube defining a fluid tight inner passageway extending longitudinally therethrough, the elongate tube including a plurality of segments releasably coupled together, the plurality of segments being configured to be selectively removed from a proximal end of the elongate tube to reduce a longitudinal length of the elongate tube;
    a collar having a central opening and being configured to receive the elongate tube through the central opening such that each of the plurality of segments proximal to the collar is removable from a remainder of the plurality of segments to reduce the longitudinal length of the elongate tube; and
    a housing configured to mate to the collar, the housing having at least one seal disposed therein that is configured to form at least one of a seal around an instrument disposed through the housing and a seal across the housing when no instrument is disposed therethrough.

12. The adjustable access device of claim 11, wherein the plurality of segments proximal to the collar are removable as a singular unit from the remainder of the plurality of segments by rotating the plurality of segments proximal to the collar as a singular unit about a longitudinal axis of the elongate tube relative to the remainder of the plurality of segments.

13. The adjustable access device of claim 11, wherein each of the plurality of segments has a distally tapering shape such that when a distal end of one of the plurality of segments is inserted into a proximal end of another one of the plurality of segments a fluid tight seal formed between the one of the plurality of segments and the other one of the plurality of segments.

14. The adjustable access device of claim 11, further comprising one or more additional segments configured to be selectively attached to a terminal end of the elongate tube to increase the longitudinal length of the elongate tube.

15. The adjustable access device of claim 11, further comprising an anchor coupled to a distal most one of the plurality of segments.

16. The adjustable access device of claim 15, further comprising an actuator extending inside the elongate tube along a longitudinal length thereof, wherein the actuator is configured to be actuated to move the anchor from a first configuration in which the anchor has a first outer diameter to a second configuration in which the anchor has a second outer diameter that is greater than the first outer diameter.

17. An adjustable access device, comprising:
- a cannula comprising a plurality of segments removably coupled to one another such that a mating connection between each of the plurality of segments forms a fluid tight seal and such that a length of the cannula is adjustable, the cannula defining a working channel extending therethrough for receiving an instrument; and
- a collar slidably disposed on the cannula and configured to selectively engage one of the plurality of segments to allow adjustment of a distance between the collar and a distal end of the cannula;
- wherein each of the segments proximal to the one of the plurality of segments engaged by the collar are removable from the one of the plurality of segments engaged by the collar and each of the plurality of segments distal to the collar.

18. The adjustable access device of claim 17, wherein the collar is slidably disposed on an outer perimeter of the cannula.

* * * * *